(12) United States Patent
   Suzuki

(10) Patent No.: US 11,069,739 B2
(45) Date of Patent: Jul. 20, 2021

(54) IMAGING DEVICE AND ELECTRONIC APPARATUS

(71) Applicant: SONY SEMICONDUCTOR SOLUTIONS CORPORATION, Kanagawa (JP)

(72) Inventor: Misao Suzuki, Kanagawa (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 163 days.

(21) Appl. No.: 16/483,921

(22) PCT Filed: Feb. 7, 2018

(86) PCT No.: PCT/JP2018/004155
§ 371 (c)(1),
(2) Date: Aug. 6, 2019

(87) PCT Pub. No.: WO2018/155183
PCT Pub. Date: Aug. 30, 2018

(65) Prior Publication Data
US 2019/0393261 A1    Dec. 26, 2019

(30) Foreign Application Priority Data

Feb. 21, 2017 (JP) .............................. JP2017-030375

(51) Int. Cl.
*H01L 27/146* (2006.01)
*H01L 31/0304* (2006.01)
(Continued)

(52) U.S. Cl.
CPC .. *H01L 27/14649* (2013.01); *H01L 27/14607* (2013.01); *H01L 31/03046* (2013.01);
(Continued)

(58) Field of Classification Search
CPC ......... H01L 27/14649; H01L 27/14607; H01L 31/03046; H01L 31/1037; H01L 27/14636;
(Continued)

(56) References Cited

U.S. PATENT DOCUMENTS

2010/0060769 A1    3/2010 Inuiya
2011/0102620 A1    5/2011 Sakano et al.
(Continued)

FOREIGN PATENT DOCUMENTS

JP    2010-067827    3/2010
JP    2010-245499    10/2010
(Continued)

OTHER PUBLICATIONS

International Search Report prepared by the Japan Patent Office dated Mar. 13, 2018, for International Application No. PCT/JP2018/004155.

*Primary Examiner* — Thanhha S Pham
(74) *Attorney, Agent, or Firm* — Sheridan Ross P.C.

(57) ABSTRACT

Provided is an imaging device including: a pixel region including a first photoelectric converter; an outside-pixel region including a second photoelectric converter coupled to a predetermined electric potential; and a circuit substrate having one surface on which the first photoelectric converter and the second photoelectric converter are provided, and including a peripheral circuit electrically coupled to the first photoelectric converter.

18 Claims, 25 Drawing Sheets

(51) Int. Cl.
  *H04N 5/374*  (2011.01)
  *H04N 5/33*   (2006.01)
  *A61B 1/04*   (2006.01)
(52) U.S. Cl.
  CPC .............. *H04N 5/33* (2013.01); *H04N 5/374*
         (2013.01); *A61B 1/04* (2013.01)
(58) Field of Classification Search
  CPC ........ H01L 27/14618; H01L 27/14694; H04N
       5/33; H04N 5/374; H04N 5/22; A61B
       1/045; Y02E 10/544
  See application file for complete search history.

(56)        References Cited

U.S. PATENT DOCUMENTS

| | | |
|---|---|---|
| 2012/0086095 A1 | 4/2012 | Nishiyama et al. |
| 2014/0217475 A1* | 8/2014 | Ohta ................. H01L 27/14612 |
| | | 257/231 |
| 2015/0041871 A1 | 2/2015 | Sakano et al. |
| 2015/0097966 A1 | 4/2015 | Nishiyama |
| 2016/0249000 A1 | 8/2016 | Esumi |
| 2017/0237916 A1 | 8/2017 | Sakano et al. |

FOREIGN PATENT DOCUMENTS

| | | |
|---|---|---|
| JP | 2011-097418 | 5/2011 |
| JP | 2014-003116 | 1/2014 |
| JP | 2014-127499 | 7/2014 |
| JP | 2016-096233 | 5/2016 |
| WO | WO 2010/116974 | 10/2010 |

* cited by examiner

IMAGING DEVICE AND ELECTRONIC APPARATUS

CROSS REFERENCE TO RELATED APPLICATIONS

This application is a national stage application under 35 U.S.C. 371 and claims the benefit of PCT Application No. PCT/JP2018/004155 having an international filing date of 7 Feb. 2018, which designated the United States, which PCT application claimed the benefit of Japanese Patent Application No. 2017-030375 filed 21 Feb. 2017, the entire disclosures of each of which are incorporated herein by reference.

TECHNICAL FIELD

The present technology relates to an imaging device and an electronic apparatus that are used in, for example, an infrared sensor or the like.

BACKGROUND ART

In recent years, imaging devices (infrared sensors) having sensitivity to an infrared region have been commercialized. For example, PTL 1 describes such an infrared sensor using a group III-V semiconductor, such as indium gallium arsenide (InGaAs), as a photoelectric converter. Infrared rays are absorbed by this photoelectric converter, thereby causing an electric charge to be generated (photoelectric conversion to be performed).

CITATION LIST

Patent Literature

PTL 1: Japanese Unexamined Patent Application Publication No. 2014-127499

SUMMARY OF THE INVENTION

Such an imaging device has been desired to suppress degradation of image quality.

Therefore, it is desirable to provide an imaging device and an electronic apparatus that make it possible to suppress degradation of image quality.

An imaging device according to an embodiment of the present technology includes: a pixel region including a first photoelectric converter; an outside-pixel region including a second photoelectric converter coupled to a predetermined electric potential; and a circuit substrate having one surface on which the first photoelectric converter and the second photoelectric converter are provided, and including a peripheral circuit electrically coupled to the first photoelectric converter.

An electronic apparatus according to an embodiment of the present technology includes the imaging device according to the embodiment of the present technology.

In the imaging device and the electronic apparatus according to the respective embodiments of the present technology, the second photoelectric converter coupled to the predetermined electric potential is provided in the outside-pixel region; therefore, light generated in the outside-pixel region and light that has entered the outside-pixel region are subjected to photoelectric conversion separately from light that has entered the pixel region, and are discharged to the predetermined electric potential.

According to the imaging device and the electronic apparatus of the respective embodiments of the present technology, the second photoelectric converter coupled to the predetermined electric potential is provided in the outside-pixel region; therefore, it is possible to suppress the influences of the light generated in the outside-pixel region and the light that has entered the outside-pixel region on the pixel region. Accordingly, it is possible to suppress degradation of the image quality. It is to be noted that the effects described here are not necessarily limitative, and may be any of effects described in the present disclosure.

MODES FOR CARRYING OUT THE INVENTION

In the following, some embodiments of the present technology are described in detail with reference to the drawings. It is to be noted that description is given in the following order.
1. First Embodiment (An example of an imaging device with a second photoelectric converter provided in an outside-pixel region)
2. Modification Example 1 (An example where the second photoelectric converter is supplied with a predetermined electric potential from a transparent electrode)
3. Modification Example 2 (An example where a pixel region and an outside-pixel region have respective separate transparent electrodes)
4. Modification Example 3 (An example where the pixel region and the outside-pixel region have respective separate transparent electrodes, and the second photoelectric converter is supplied with a predetermined electric potential from the transparent electrode)
5. Modification Example 4 (An example where only the pixel region is provided with the transparent electrode)
6. Modification Example 5 (An example where a first photoelectric converter and the second photoelectric converter are continuous)
7. Second Embodiment (An example where the first photoelectric converter and the second photoelectric converter are each a photodiode)
8. Application Example (An example of an electronic apparatus)
9. Practical Application Example 1 (An example of an in-vivo information acquisition system)
10. Practical Application Example 2 (An example of a mobile body control system)

1. First Embodiment

Figure 1:
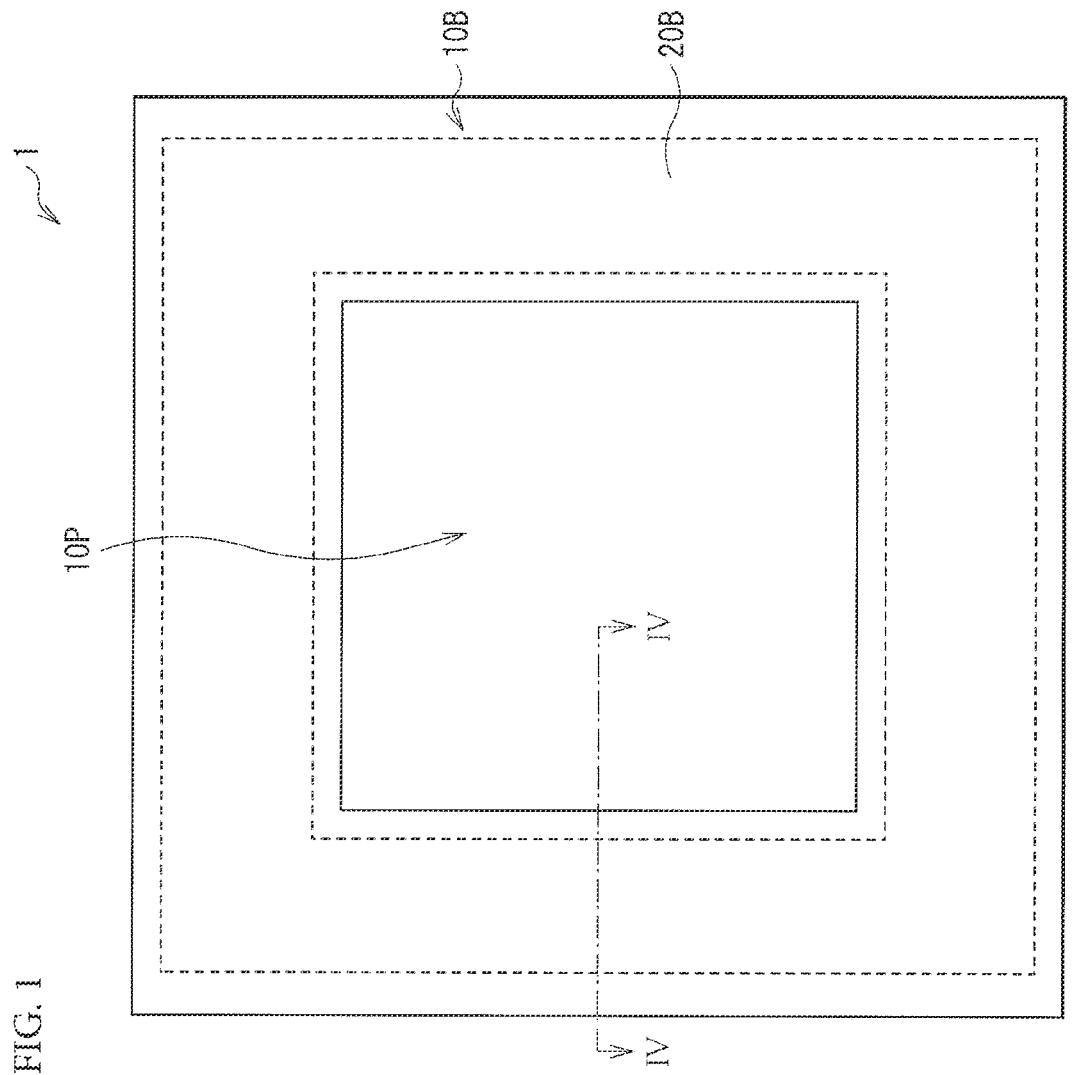
FIG. 1 is a plan view of a schematic configuration of an imaging device according to a first embodiment of the present technology.

[Configuration of Imaging Device]
FIG. 1 illustrates a schematic planar configuration of an imaging device (an imaging device 1) according to a first embodiment of the present technology. The imaging device 1 is, for example, an infrared image sensor, and has sensitivity to light of, for example, a wavelength of 800 nm or more as well. This imaging device 1 is provided with, for example, a quadrangular pixel region 10P and an outside-pixel region 10B that lies outside the pixel region 10P. The outside-pixel region 10B is provided with a peripheral circuit 20B for driving of the pixel region 10P.

Figure 2:
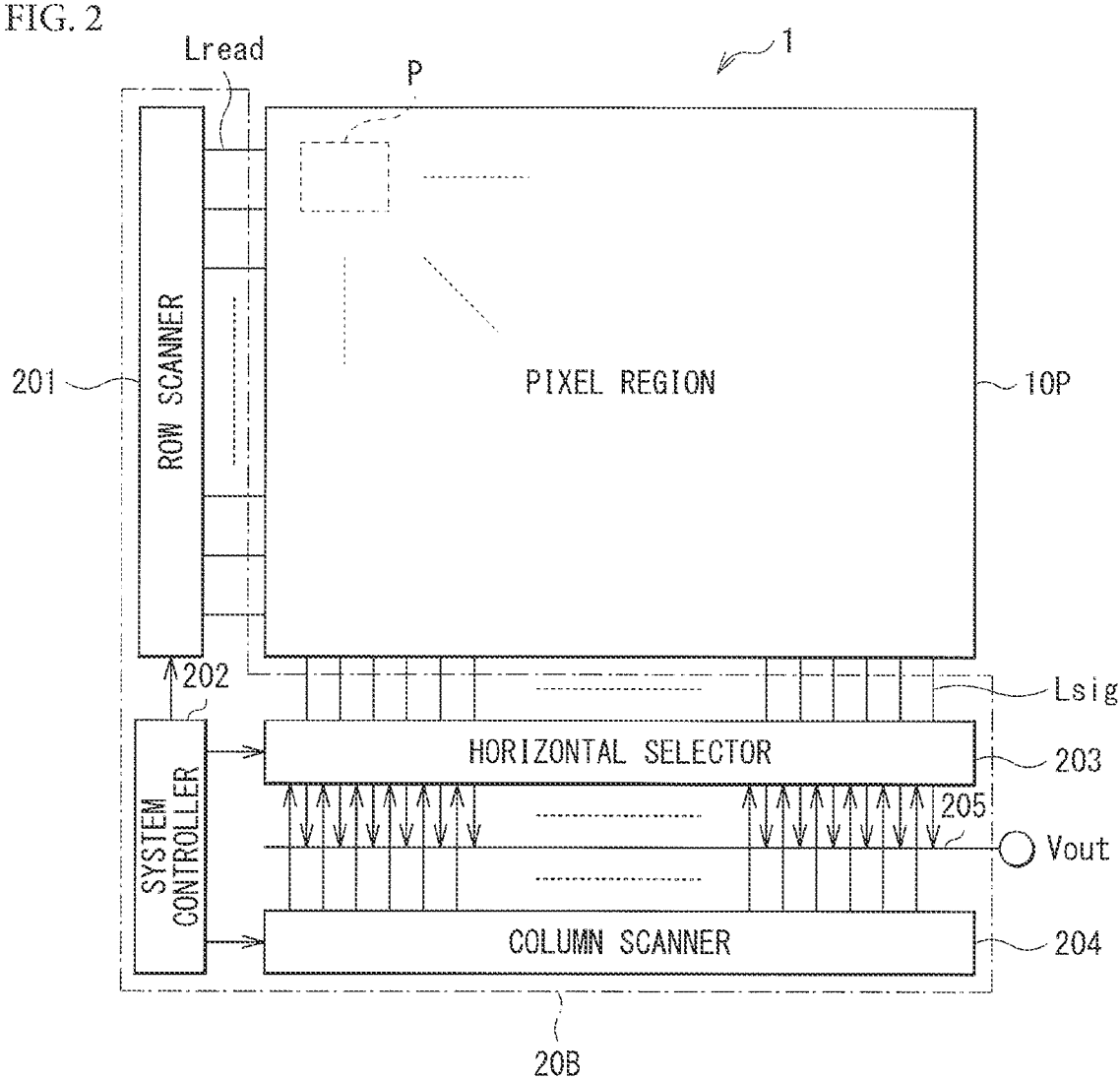
FIG. 2 is a block diagram illustrating an example of a functional configuration of the imaging device illustrated in FIG. 1.

FIG. 2 illustrates a functional configuration of the imaging device 1. The pixel region 10P of the imaging device 1 is provided with, for example, a plurality of light-receiving unit regions (pixels P) arranged two-dimensionally. The peripheral circuit 20B includes, for example, a row scanner 201, a horizontal selector 203, a column scanner 204, and a system controller 202.

For example, a pixel drive line Lread (for example, a row selection line and a reset control line) is wired with the pixel P for each pixel row, and a vertical signal line Lsig is wired with the pixel P for each pixel column. The pixel drive line Lread transmits a drive signal for signal reading from the pixel P. One end of the pixel drive line Lread is coupled to an output terminal corresponding to each row of the row scanner 201.

The row scanner 201 is a pixel driver that includes a shift register, an address decoder, etc., and drives each pixel P of the pixel region 10P, for example, on a row-by-row basis. A signal outputted from each pixel P of a pixel row selected and scanned by the row scanner 201 is supplied to the horizontal selector 203 through each vertical signal line Lsig. The horizontal selector 203 includes an amplifier, a horizontal selection switch, etc. that are provided for each vertical signal line Lsig.

The column scanner 204 includes a shift register, an address decoder, etc., and sequentially drives the horizontal selection switches of the horizontal selector 203 while scanning. Through this selective scanning by the column scanner 204, a signal of each pixel transmitted through a corresponding vertical signal line Lsig is sequentially outputted to a horizontal signal line 205, and is inputted to an unillustrated signal processor or the like through the horizontal signal line 205.

The system controller 202 receives a clock given from the outside or data instructing an operation mode, etc., and outputs data such as internal information of the imaging device 1. Furthermore, the system controller 202 includes a timing generator that generates various timing signals, and performs drive control of the row scanner 201, the horizontal selector 203, and the column scanner 204 on the basis of the various timing signals generated by the timing generator.

Figure 3:
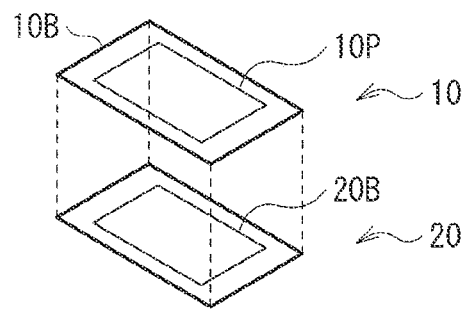
FIG. 3 is an exploded perspective view of a schematic configuration of the imaging device illustrated in FIG. 1.

FIG. 3 is an exploded perspective view schematically illustrating a configuration of the imaging device 1. In the imaging device 1, a semiconductor substrate 10 having the pixel region 10P and a circuit substrate 20 for driving of the pixels P of the pixel region 10P are stacked on each other. The circuit substrate 20 is provided with a circuit that amplifies a signal electric charge subjected to photoelectric conversion performed by the semiconductor substrate 10 or converts the signal electric charge from analog to digital for outputting. This circuit substrate 20 is provided with the peripheral circuit 20B.

Figure 4:
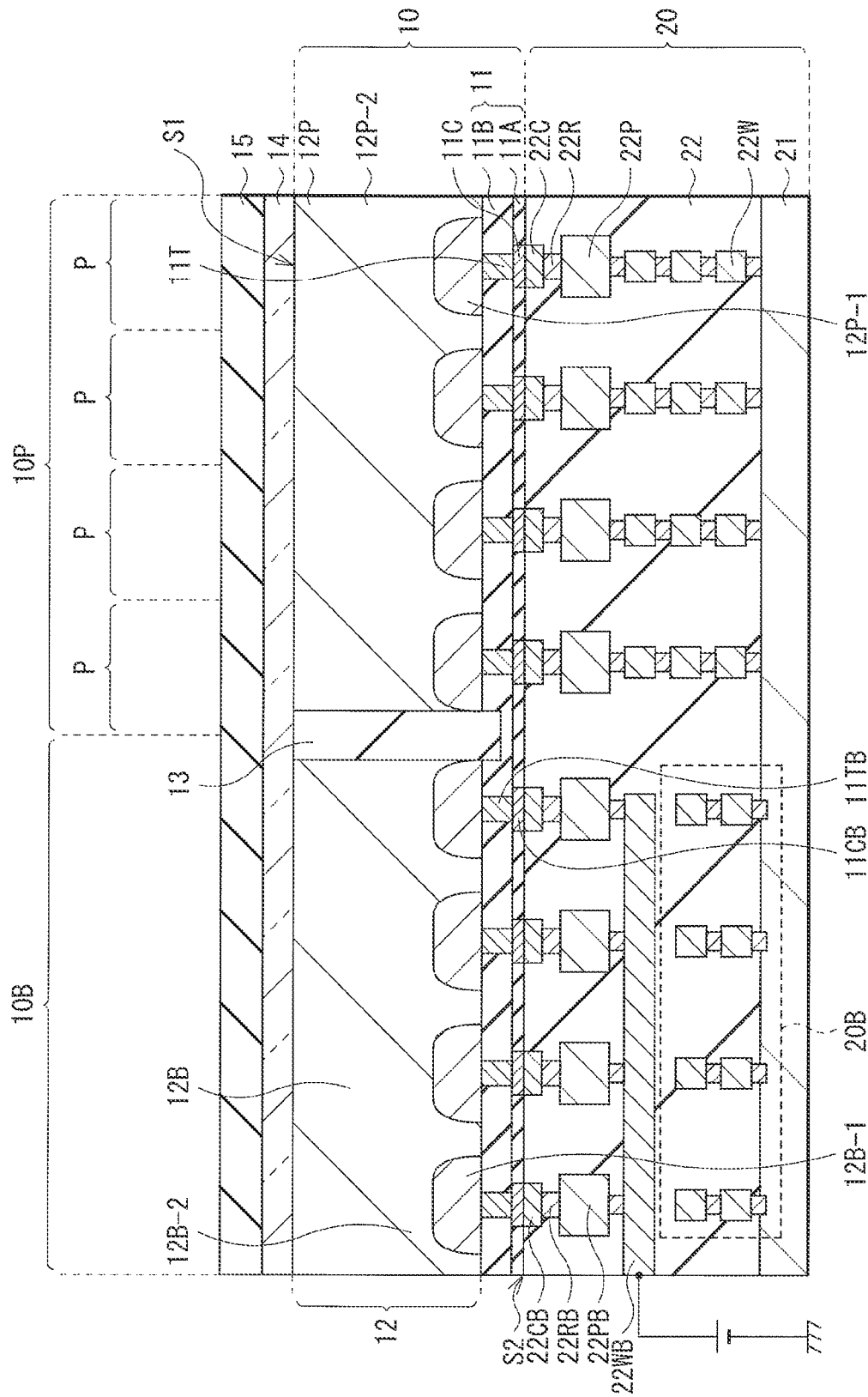
FIG. 4 schematically illustrates a cross-sectional configuration taken along a line IV-IV illustrated in FIG. 1

FIG. 4 schematically illustrates a cross-sectional configuration of the imaging device 1 taken along a line IV-IV illustrated in FIG. 1. The semiconductor substrate 10 has a light incident surface S1; a surface opposite to this light incident surface S1 is a joint surface (a joint surface S2) to the circuit substrate 20. The semiconductor substrate 10 serves to perform photoelectric conversion on, for example, incident light such as light of a wavelength in an infrared region for each pixel P, and includes a protective layer 11 and a photoelectric conversion layer 12 in order from a position closer to the joint surface S2. The photoelectric conversion layer 12 is provided with a separation film 13 that separates the pixel region 10P and the outside-pixel region 10B from each other. On the light incident surface S1 of the semiconductor substrate 10 are provided with a transparent electrode 14 and a passivation film 15 in this order. The circuit substrate 20 is provided with a readout integrated circuit (ROIC) that reads out a signal electric charge generated in the semiconductor substrate 10. Respective configurations of the components are described below.

The protective layer 11 has, for example, a stacked structure of a protective layer 11A and a protective layer 11B. The protective layer 11A is a layer that configures the joint surface S2, and this protective layer 11A is in contact with the circuit substrate 20. The protective layer 11A is provided with connection layer 11C for respective pixels P. The protective layer 11A of the outside-pixel region 10B is provided with connection layers 11CB, for example, at the same pitch as the connection layers 11C of the pixel region 10P. The protective layer 11B is provided between the protective layer 11A and the photoelectric conversion layer 12. This protective layer 11B is provided with through electrodes 11T for respective pixels P. The protective layer 11B of the outside-pixel region 10B is provided with through electrodes 11TB, for example, at the same pitch as the through electrodes IT of the pixel region 10P. The through electrodes 11T and 11TB are each an electrode to be supplied with a voltage to read out an electric charge (for example, a hole) generated in the photoelectric conversion layer 12, and are in contact with the connection layers 11C and 11CB, respectively. That is, a signal electric charge generated in the photoelectric conversion layer 12 moves to the circuit substrate 20 through the through electrode 11T or 11TB and the connection layer 11C or 11CB.

The protective layer 11 may include, for example, an inorganic insulating material. Examples of this inorganic insulating material include silicon nitride (SiN), aluminum oxide ($Al_2O_3$), silicon oxide ($SiO_2$), and hafnium oxide ($HfO_2$). The protective layer 11A and the protective layer 11B may include the same material, or may include different materials.

For example, a simple substance of any one of titanium (Ti), tungsten (W), titanium nitride (TiN), platinum (Pt), gold (Au), germanium (Ge), palladium (Pd), zinc (Zn), nickel (Ni), aluminum (Al), and the like, or an alloy containing at least one of these may be used for the through electrodes 11T and 11TB and the connection layers 11C and 11CB. The through electrodes 11T and 11TB and the connection layers 11C and 11CB may be a single layer film, or may be a multilayer film.

The photoelectric conversion layer 12 absorbs light of a predetermined wavelength (for example, light of a wavelength in an infrared region of a wavelength of 900 nm to 1700 nm) and generates a signal electric charge, and includes, for example, a compound semiconductor such as a group III-V semiconductor. Examples of the group III-V semiconductor used for the photoelectric conversion layer 12 include indium gallium arsenide (InGaAs). The composition of InGaAs is, for example, $In_xGa_{(1-x)}As$ (x: $0<x\leq1$). To increase the sensitivity to the infrared region, x preferably satisfies $x\geq0.4$. The photoelectric conversion layer 12 may include mercury cadmium telluride (HgCdTe), indium antimonide (InSb), or the like.

The photoelectric conversion layer 12 includes a first photoelectric converter 12P provided in the pixel region 10P and a second photoelectric converter 12B provided in the outside-pixel region 10B; the first photoelectric converter 12P and the second photoelectric converter 12B are electrically separated from each other by the separation film 13. In the present embodiment, this second photoelectric converter 12B of the outside-pixel region 10B is coupled to a predetermined electric potential, and light that has entered the second photoelectric converter 12B is processed separately from light that has entered the first photoelectric converter 12P. As described in detail later, this makes it possible to suppress influences of light generated in the outside-pixel region 10B (for example, light E in FIG. 8 described later) and light that has entered the outside-pixel region 10B (for example, light L1 in FIG. 9 described later) on the pixel region 10P.

Figure 5:
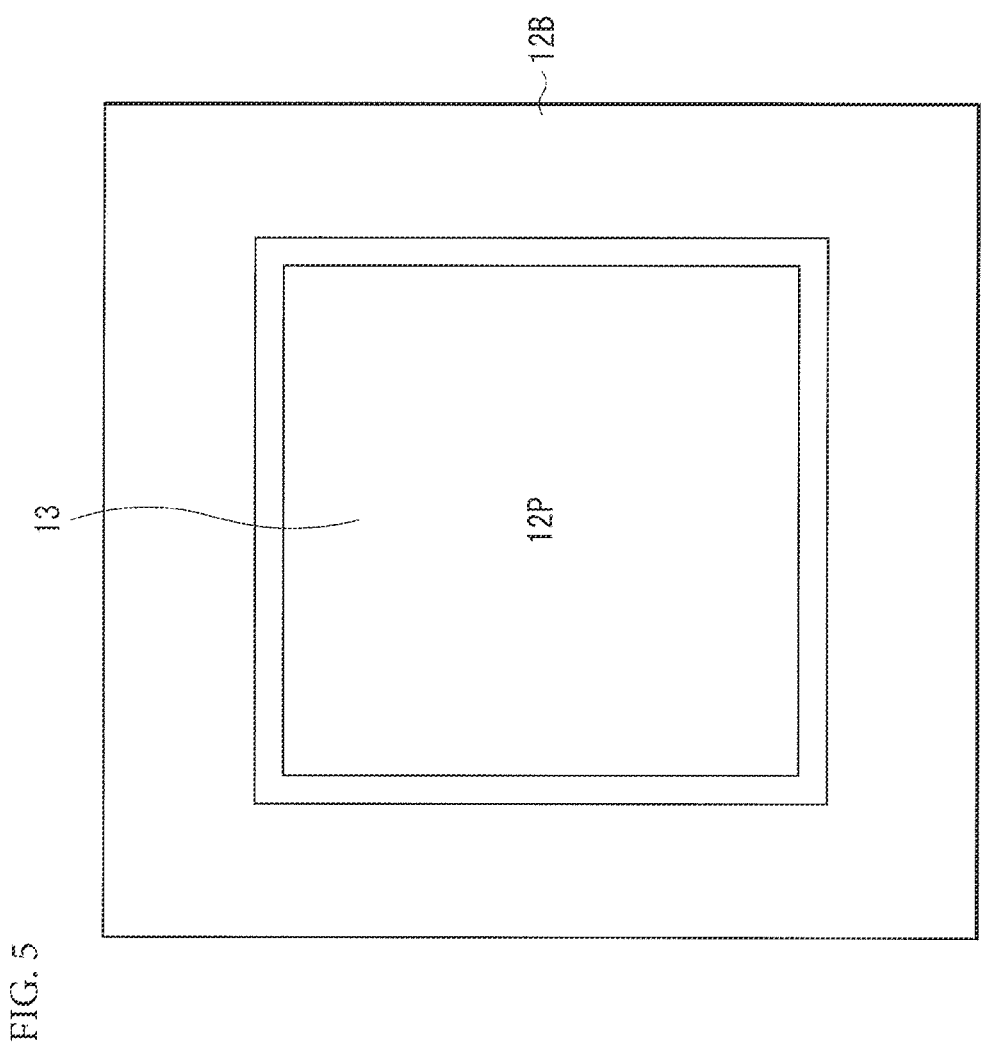
FIG. 5 is a plan view schematically illustrating a configuration of a photoelectric conversion layer illustrated in FIG. 4.

FIG. 5 illustrates a schematic planar configuration of the photoelectric conversion layer 12. For example, the second photoelectric converter 12B is provided to surround the first photoelectric converter 12P having a quadrangular shape in a plan view. The second photoelectric converter 12B may not necessarily be provided outside all sides of the first photoelectric converter 12P: it is sufficient that the second photoelectric converter 12B may be provided in at least a portion of the outside-pixel region 10B. The second photoelectric converter 12B may be preferably provided in a region that overlaps the peripheral circuit 20B in a plan view (FIG. 4). One reason for this is that this makes it possible to efficiently process light generated due to the peripheral circuit 20B (light E in FIG. 8 described later). For example, the second photoelectric converter 12B is provided more extensively than the peripheral circuit 20B in a plan view, and covers the peripheral circuit 20B.

A sensitivity wavelength range of the second photoelectric converter 12B is, for example, the same as a sensitivity wavelength range of the first photoelectric converter 12P, and the first photoelectric converter 12P and the second photoelectric converter 12B (the photoelectric conversion layer 12) each absorb light of a wavelength in the infrared region and perform photoelectric conversion on the light. The sensitivity wavelength range of the second photoelectric converter 12B may be wider than the sensitivity wavelength range of the first photoelectric converter 12P. A constituent material of the second photoelectric converter 12B may be different from a constituent material of the first photoelectric converter 12P, but may be preferably the same. When the first photoelectric converter 12P and the second photoelectric converter 12B are the same in their constituent materials and their compositions, it is possible for the first photoelectric converter 12P and the second photoelectric converter 12B to be formed by the same process. That is, it is possible to form the second photoelectric converter 12B easily. Furthermore, by using the same constituent material as that of the first photoelectric converter 12P in the second photoelectric converter 12B, it becomes possible to make the second photoelectric converter 12B have durability equivalent to that of the first photoelectric converter 12P.

First electrically-conductive type regions 12P-1 are provided near the protective layer 11 of the first photoelectric converter 12P for respective pixels P. Of the first photoelectric converter 12P, a portion other than the first electrically-conductive type regions 12P-1 is a second electrically-conductive type region 12P-2. First electrically-conductive type regions 12B-1 are provided near the protective layer 11 of the second photoelectric converter 12B, for example, at the same pitch as the first electrically-conductive type regions 12P-1 of the pixel region 10P. Of the second photoelectric converter 12B, a portion other than the first electrically-conductive type regions 12B-1 is a second electrically-conductive type region 12B-2.

The first electrically-conductive type regions 12P-1 and 12B-1 are each a region to which one of electric charges generated in the photoelectric conversion layer 12 moves, and are coupled to the through electrodes 11T and 11TB, respectively. These first electrically-conductive type regions 12P-1 and 12B-1 contain, for example, a p-type impurity, for example, such as zinc (Zn). The second electrically-conductive type regions 12P-2 and 12B-2 contain, for example, an n-type impurity such as silicon (Si). The second electrically-conductive type regions 12P-2 and 12B-2 may include an intrinsic semiconductor (may be an i-type semiconductor region). In the first photoelectric converter 12P and the second photoelectric converter 12B, p-n junctions or p-i-n junctions are provided at interfaces between the first electrically-conductive type regions 12P-1 and 12B-1 and the second electrically-conductive type regions 12P-2 and 12B-2, respectively.

The separation film 13 is provided at least in the photoelectric conversion layer 12. The separation film 13 penetrates the photoelectric conversion layer 12, for example, and is also provided in a portion of the protective layer 11 in a thickness direction. The separation film 13 is provided, for example, to surround the first photoelectric converter 12P in a frame shape (FIG. 5). This separation film 13 serves to electrically separate the first photoelectric converter 12P and the second photoelectric converter 12B from each other, and includes, for example, an insulating material such as silicon oxide ($SiO_2$).

The transparent electrode 14 is in contact with the photoelectric conversion layer 12 across the first photoelectric converter 12P and the second photoelectric converter 12B. That is, a portion (a first electrode) of the transparent electrode 14 is opposed to the circuit substrate 20 with the first photoelectric converter 12P being interposed therebetween, and another portion or the entire (a second electrode) of the transparent electrode 14 is opposed to the circuit substrate 20 with the second photoelectric converter 12B being interposed therebetween. In this example, the transparent electrode 14 on the first photoelectric converter 12P and the transparent electrode 14 on the second photoelectric converter 12B are integrally provided. This transparent electrode 14 serves to discharge an unnecessary electric charge generated in the photoelectric conversion layer 12, and is electrically coupled to each of the first photoelectric converter 12P and the second photoelectric converter 12B. When, for example, a hole, of an electric charge generated in the first photoelectric converter 12P, is read out as a signal electric charge by the circuit substrate 20, electrons generated in the first photoelectric converter 12P and the second photoelectric converter 12B are discharged through this transparent electrode 14.

The transparent electrode 14 includes an electrically-conductive layer that transmits incident light such as, for example, infrared rays. For example, a simple substance of any one of titanium (Ti), tungsten (W), titanium nitride (TiN), platinum (Pt), gold (Au), germanium (Ge), nickel (Ni), and aluminum (Al), or an alloy containing at least one of these may be used for the transparent electrode 14. It is preferable to use a material having a high transmittance of light of a wavelength in the infrared region, for example, ITiO ($In_2O_3$—$TiO_2$) for the transparent electrode 14. Besides those mentioned above, indium tin oxide (ITO), tin (Sn), tin oxide (SnO2), tungsten-doped indium oxide (IWO), indium-zinc composite oxide (IZO), zinc-doped aluminum oxide (AZO), zinc-doped gallium oxide (GZO), magnesium-and-zinc-doped aluminum oxide (AlMgZnO), indium-gallium composite oxide (IGO), In—GaZnO4 (IGZO), fluorine-doped tin oxide (FTO), zinc oxide (ZnO), boron-doped zinc oxide, InSnZnO, and the like may be used for the transparent electrode 14.

The passivation film 15 serves to planarize the light incident surface Si of the semiconductor substrate 10, and includes, for example, an inorganic insulating material. For example, an inorganic insulating material such as silicon nitride (SiN), aluminum oxide ($Al_2O_3$), silicon oxide ($SiO_2$), and hafnium oxide ($HfO_2$) may be used for the passivation film 15. A color filter and an on-chip lens, etc. may be provided on the passivation film 15.

The circuit substrate 20 includes a support substrate 21 and an interlayer insulating layer 22. The support substrate 21 includes, for example, a silicon (Si) substrate. The interlayer insulating layer 22 is provided between the support substrate 21 and the protective layer 11 (the semiconductor substrate 10). This interlayer insulating layer 22 is provided with an ROIC to read out a signal from each pixel P. The pixel region 10P of the interlayer insulating layer 22 is provided with a connection layer 22C, a readout electrode 22R, a pixel circuit 22P, and a plurality of wiring lines 22W, for example, in order from a position closer to the semiconductor substrate 10. The outside-pixel region 10B of the interlayer insulating layer 22 is provided with a connection layer 22CB, a readout electrode 22RB, a pixel circuit 22PB, a wiring line 22WB, and the peripheral circuit 20B, for example, in order from a position closer to the semiconductor substrate 10.

The connection layer 22C is provided for each pixel P, and is in contact with the connection layer 11C of the semiconductor substrate 10. The readout electrode 22R serves to electrically couple the connection layer 22C and the pixel circuit 22P to each other, and is provided for each pixel P. The pixel circuit 22P provided for each pixel P is electrically coupled to the plurality of wiring lines 22W. Therefore, a signal electric charge generated in the first photoelectric converter 12P is read out from the connection layer 11C by the ROIC through the connection layer 22C and the readout electrode 22R.

The connection layer 22CB, the readout electrode 22RB, and the pixel circuit 22PB of the outside-pixel region 10B are provided, for example, at the same pitch as the pixel region 10P. The connection layer 22CB is in contact with the connection layer 11CB of the semiconductor substrate 10. The readout electrode 22RB serves to electrically couple the connection layer 22CB and the pixel circuit 22PB to each other. The plurality of pixel circuits 22PB are coupled to the same wiring line 22WB. The wiring line 22WB is coupled to a predetermined electric potential, for example, such as a power source of the imaging device 1 or a ground (GND) electric potential. Therefore, an electric charge generated in the second photoelectric converter 12B is discharged to the predetermined electric potential through the connection layer 11CB, the connection layer 22CB, the readout electrode 22RB, the pixel circuit 22PB, and the wiring line 22WB.

The peripheral circuit 20B is provided, for example, at a position that overlaps the second photoelectric converter 12B in a plan view, and is electrically coupled to the wiring lines 22W. That is, the peripheral circuit 20B is electrically coupled to the first photoelectric converter 12P through the wiring lines 22W.

Figure 6:
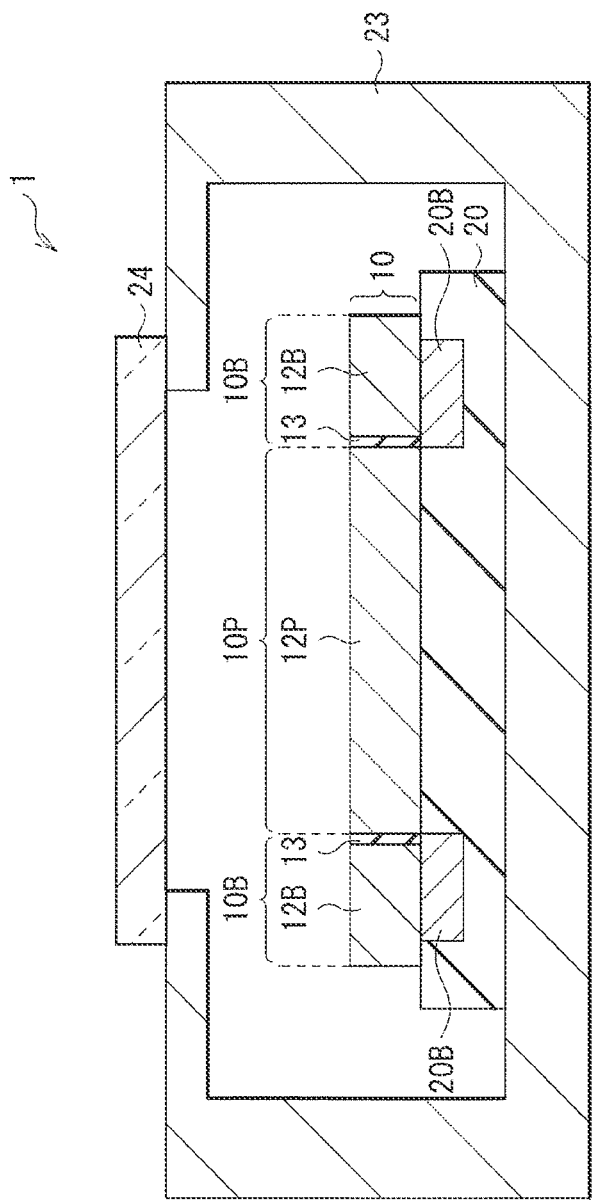
FIG. 6 is a cross-sectional view of an example of a state where the imaging device illustrated in FIG. 4 is packaged.

FIG. 6 schematically illustrates a cross-sectional configuration of the imaging device 1 housed in a package. The imaging device 1 including the semiconductor substrate 10 and the circuit substrate 20 is housed, for example, inside the package (a package 23) in this way. The package 23 includes, for example, a ceramic or a resin material, etc. The package 23 supports the circuit substrate 20, and has an opening on side of the semiconductor substrate 10. This opening is located at a position facing the pixel region 10P. The opening is covered with a sealing plate (a sealing plate 24). The sealing plate 24 includes, for example, a transparent material such as glass, and allows light to enter the photoelectric conversion layer 12 through the sealing plate 24.

[Operation of Imaging Device 1]

Figure 7:
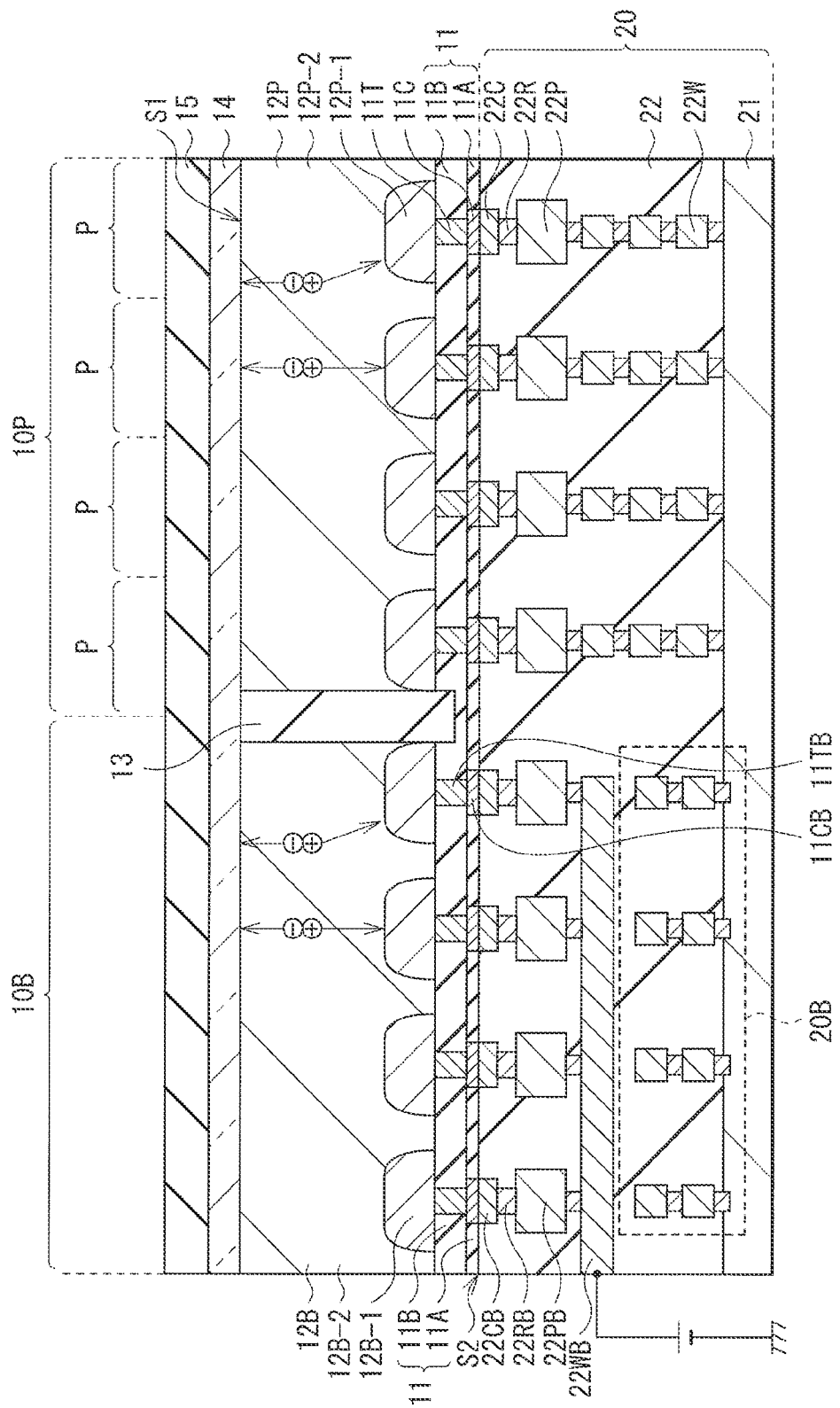
FIG. 7 is a schematic cross-sectional view for explaining an operation of the imaging device illustrated in FIG. 4.

The operation of the imaging device 1 is described with reference to FIG. 7. In the imaging device 1, when light (for example, light of a wavelength in the infrared region) enters the first photoelectric converter 12P through the sealing plate 24 (FIG. 6), the passivation film 15, and the transparent electrode 14, this light is absorbed by the first photoelectric converter 12P. This causes a pair of a hole (a hole) and an electron to be generated (photoelectric conversion to be performed) in the first photoelectric converter 12P. At this time, for example, when a predetermined voltage is applied to the through electrode 11T, the first photoelectric converter 12P has an electric potential gradient, and one electric charge (for example, the hole) of the generated electric charges moves, as a signal electric charge, to the first electrically-conductive type region 12P-1, and is collected from the first electrically-conductive type region 12P-1 into the through electrode 11T for each pixel P. This signal electric charge is read out by the ROIC of the circuit substrate 20 through the connection layers 11C and 22C.

[Workings and Effects of Imaging Device 1]

In the imaging device 1 of the present embodiment, the second photoelectric converter 12B coupled to the predetermined electric potential is provided in the outside-pixel region 10B; therefore, it is possible to suppress influences of light generated in the outside-pixel region 10B (light E in FIG. 8 described later) and light that has entered the outside-pixel region 10B (light L1 in FIG. 9 described later) on the pixel region 10P. This is described below.

Figure 8:
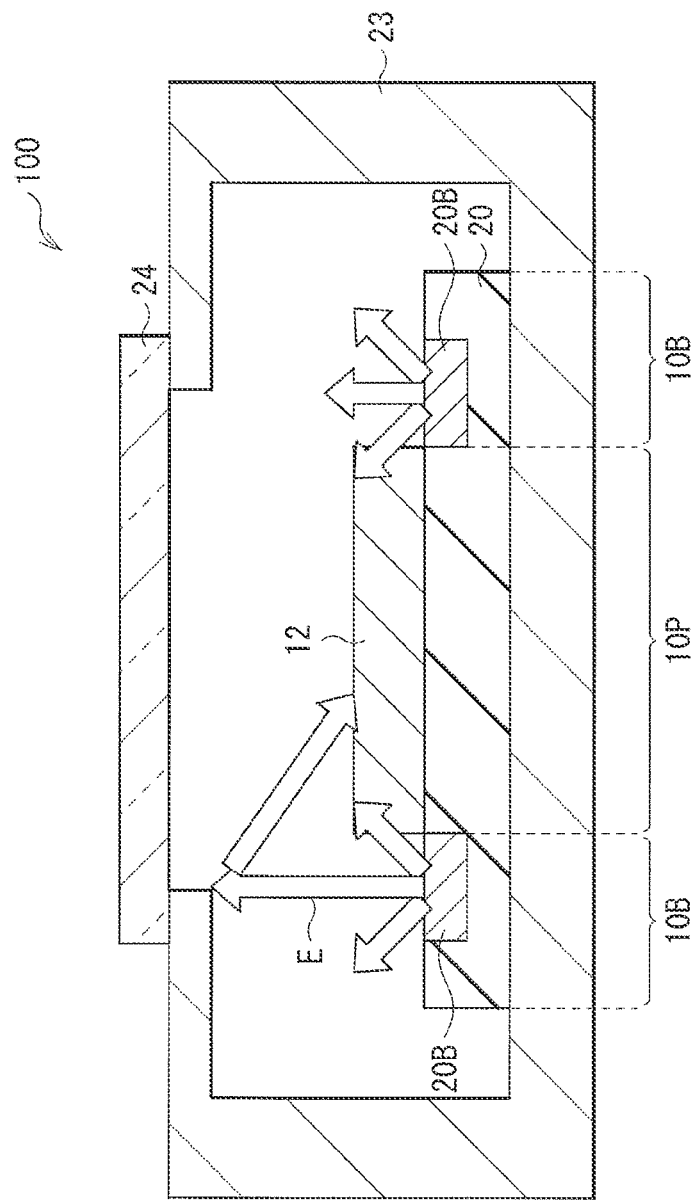
FIG. 8 is a cross-sectional view schematically illustrating a configuration of an imaging device according to a comparative example.

FIG. 8 illustrates a schematic cross-sectional configuration of an imaging device (an imaging device 100) according to a comparative example. The imaging device 100 has the photoelectric conversion layer 12 only in the pixel region 10P on the circuit substrate 20, and the outside-pixel region 10B is not provided with a photoelectric conversion layer (for example, the second photoelectric converter 12B in FIG. 4).

In such an imaging device 100, there is a possibility that light (light E) generated in the peripheral circuit 20B provided in the outside-pixel region 10B may directly enter the photoelectric conversion layer 12 of the pixel region 10P. Alternatively, there is a possibility that the light E having been reflected by the package 23 may thereafter enter the photoelectric conversion layer 12 of the pixel region 10P. The light E results from, for example, generation of a hot carrier by silicon (Si) included in the circuit substrate 20 due to a circuit operation. In an imaging device directed mainly to light of wavelengths in a visible region, even when this light E enters a pixel region, its influence on the image quality is small. However, the light E resulting from a hot carrier includes light of a wavelength in the infrared region; therefore, an imaging device directed to light of the wavelengths in the infrared region performs a photoelectric conversion process on the light E as well. That is, in the imaging device 100 used as an infrared sensor, there is a possibility that the light E may enter the photoelectric conversion layer 12 directly or by being reflected, thus considerably degrading the image quality.

As a method to prevent the light E from entering the pixel region 10P, it is conceivable to provide a reflecting member (for example, a reflecting member of a metallic material) for reflection of the light E or to provide an absorbent for absorption of the light E. However, such a method makes the configuration of the imaging device 100 complex, thus it is difficult to adopt the method. One reason for this is that, in a case where a reflecting member is provided, it is necessary to take an additional measure to prevent reflected light from the reflecting member from entering the pixel region 10P, and in a case where an absorbent is provided, it is necessary to take an additional measure against alteration of the absorbent that has absorbed the light E.

Besides the above-described methods, for example, it is also conceivable, as a method to prevent the light E from entering the pixel region 10P, to provide the peripheral circuit 20B on a substrate different from the circuit substrate 20 or to form the peripheral circuit 20B on a region sufficiently distant from the pixel region 10P. However, such methods also cause problems such as difficulty in miniaturizing the imaging device.

Figure 9:
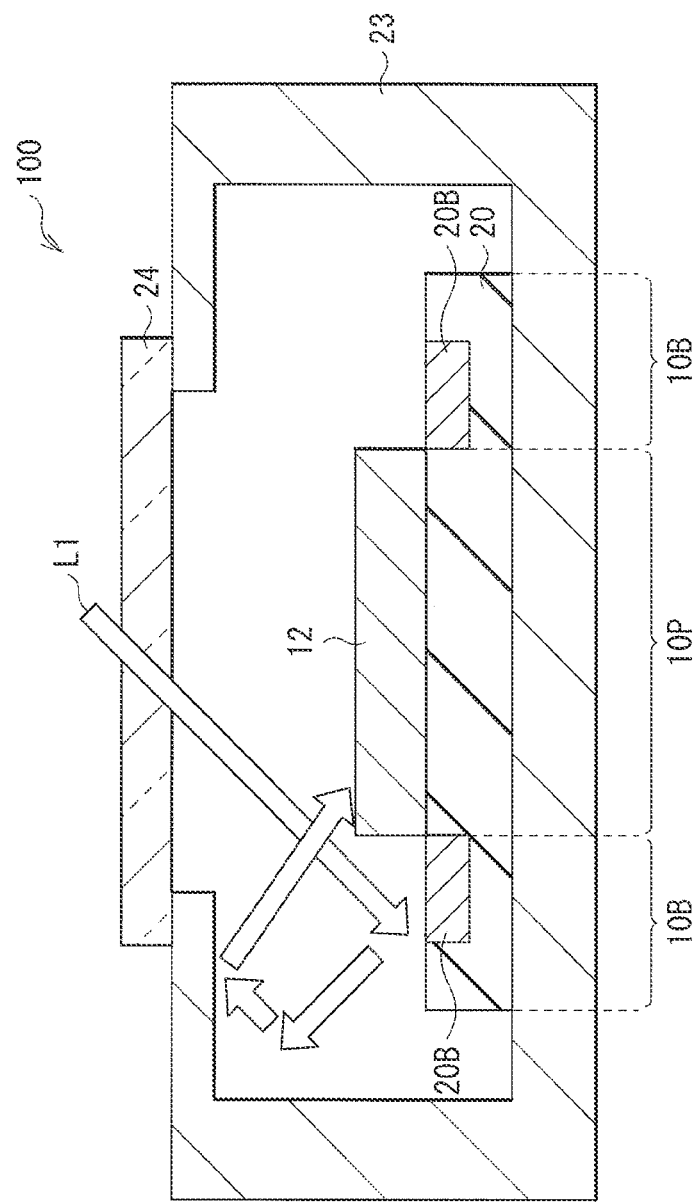
FIG. 9 is a schematic cross-sectional view for explaining light that enters an outside-pixel region of the imaging device illustrated in FIG. 8.

Furthermore, in the imaging device 100, there is a possibility that, as illustrated in FIG. 9, light (light L1) that has been incident from the outside may be reflected by the outside-pixel region 10B to enter the photoelectric conversion layer 12 of the pixel region 10P. Such light L1 causes a so-called ghost and degrades the image quality.

Meanwhile, in the imaging device 1, the second photoelectric converter 12B is provided to cover the peripheral circuit 20B of the outside-pixel region 10B: this second photoelectric converter 12B is coupled to a predetermined electric potential.

Figure 10:
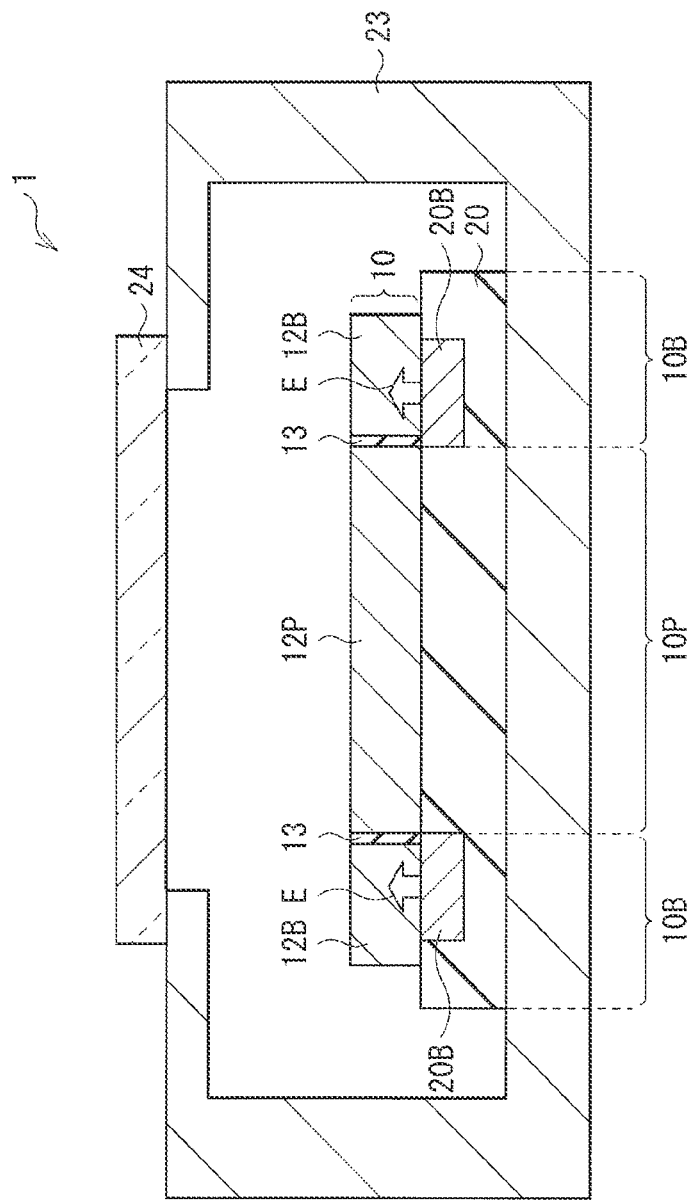
FIG. 10 is a schematic cross-sectional view (1) for explaining effects of the imaging device illustrated in FIG. 6.
Figure 11:
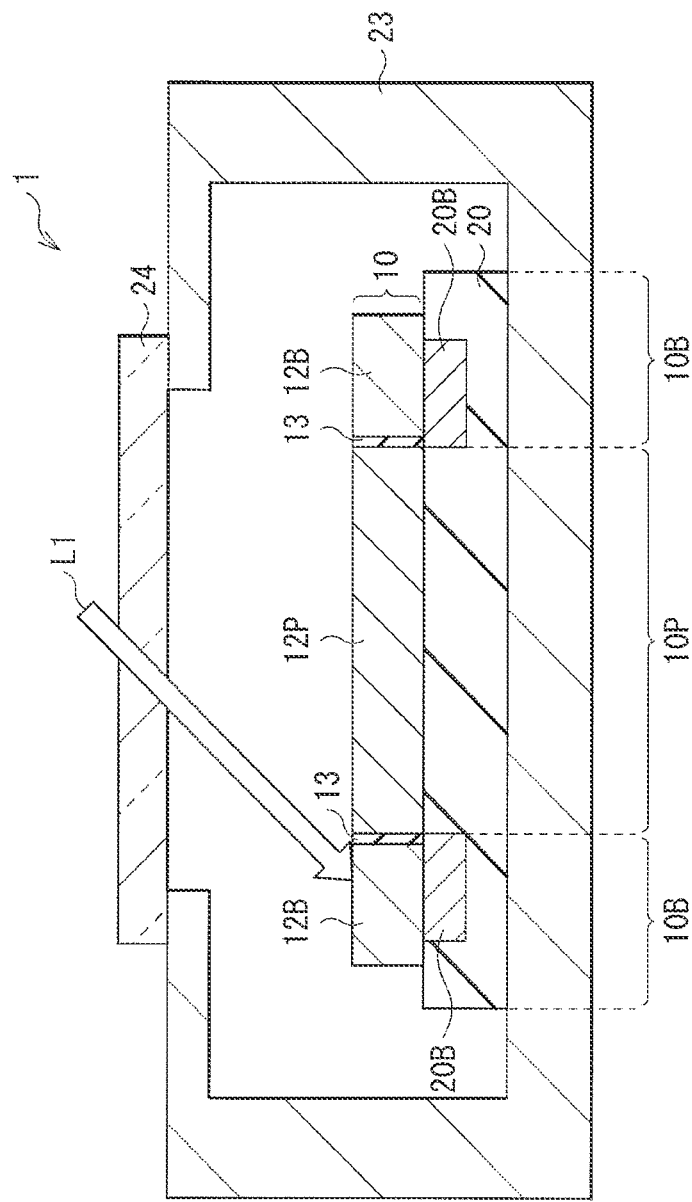
FIG. 11 is a schematic cross-sectional view (2) for explaining the effects of the imaging device illustrated in FIG. 6.

Therefore, as illustrated in FIGS. 10 and 11, it is possible to suppress the influences of the light E caused by the hot carrier and the light L1 that has been incident from the outside on the pixel region 10P. The light E and the light L1 are processed, for example, as described below.

The light E generated in the peripheral circuit 20B enters the second photoelectric converter 12B located immediately above the peripheral circuit 20B, and is absorbed by the second photoelectric converter 12B (FIG. 10). This causes a pair of a hole (a hole) and an electron to be generated (photoelectric conversion to be performed) in the second photoelectric converter 12B as illustrated in FIG. 7. At this time, for example, when a predetermined voltage is applied to the through electrode 11TB through the wiring line 22WB, the second photoelectric converter 12B has an electric potential gradient, and one electric charge (for example, the hole) of the generated electric charges moves to the first electrically-conductive type region 12B-1 and is collected from the first electrically-conductive type regions 12B-1 into the through electrode 11TB. This electric charge moves to the wiring line 22WB through the connection layers 11CB and 22CB and is discharged to the predetermined electric potential. The other electric charge (for example, the electron) generated in the second photoelectric converter 12B is discharged through the transparent electrode 14.

Furthermore, the light L1 that has entered the outside-pixel region 10B enters the second photoelectric converter 12B, and is absorbed by the second photoelectric converter 12B (FIG. 11). In a manner similar to those described above, this light L1 causes an electric charge to be generated in the second photoelectric converter 12B and to be discharged to the predetermined electric potential. That is, the light E and the light L1 are subjected to photoelectric conversion separately from light that has entered the first photoelectric converter 12P and processed; therefore, the influences of the light E and the light L1 on the pixel region 10P is suppressed. Such an imaging device 1 may not necessarily be provided with a reflecting member or an absorbing member, thus making it possible to achieve a simple configuration. Furthermore, it is possible to freely design a formation region of the peripheral circuit 20B as well, thus making it possible to miniaturize the imaging device 1.

As described above, in the present embodiment, the outside-pixel region 10B is provided with the second photoelectric converter 12B coupled to the predetermined electric potential: therefore, it is possible to suppress the influences of the light E generated in the outside-pixel region 10B and the light L1 that has entered the outside-pixel region 10B on the pixel region 10P. Accordingly, it is possible to suppress degradation of the image quality.

Modification examples of the above-described embodiment and another embodiment will be described below. In the following description, the same components as those of the above-described embodiment are denoted by the same reference numerals, and descriptions thereof are omitted where appropriate.

Modification Example 1

Figure 12:
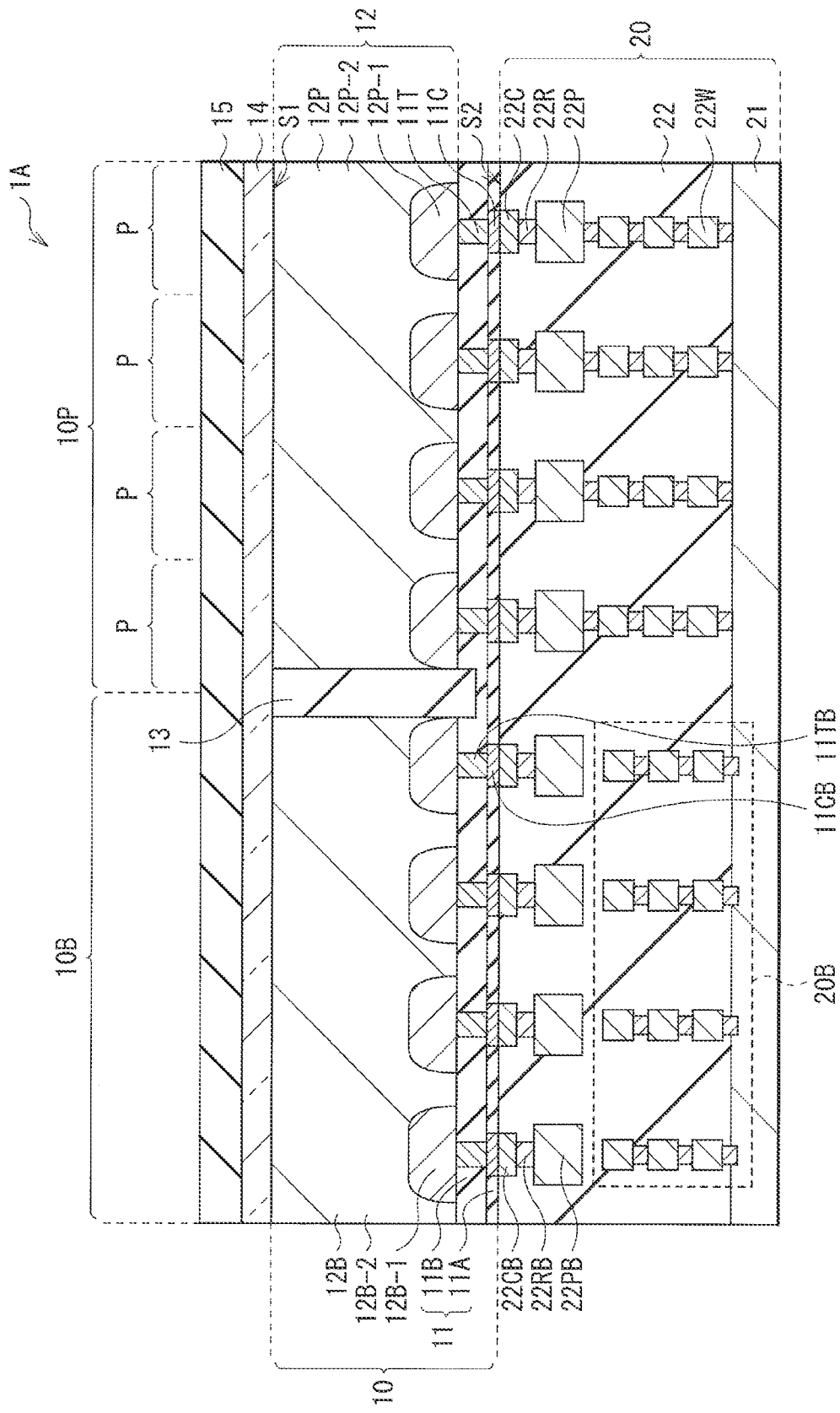
FIG. 12 is a cross-sectional view of a schematic configuration of an imaging device according to Modification Example 1.

FIG. 12 illustrates a schematic cross-sectional configuration of an imaging device (an imaging device 1A) according to Modification Example 1. In this way, the second photoelectric converter 12B may be supplied with a predetermined electric potential only from the transparent electrode 14.

In this imaging device 1A, the through electrode 11TB of the outside-pixel region 10B is not coupled to a wiring line (the wiring line 22WB in FIG. 4). That is, the second photoelectric converter 12B is not supplied with an electric potential from side of the circuit substrate 20. Therefore, an electric charge generated in the second photoelectric converter 12B is discharged to the predetermined electric potential through the transparent electrode 14.

Modification Example 2

Figure 13:
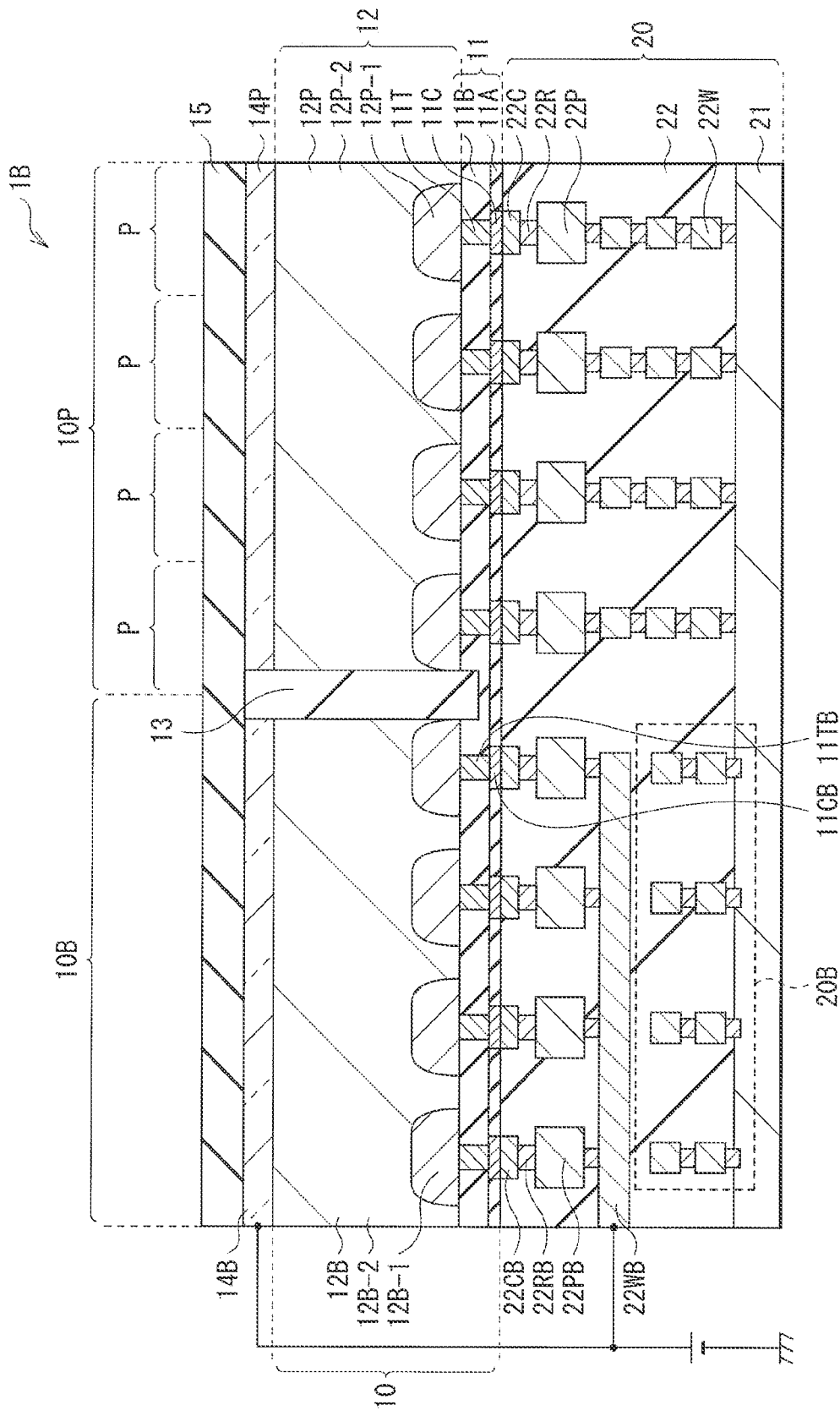
FIG. 13 is a cross-sectional view of a schematic configuration of an imaging device according to Modification Example 2.

FIG. 13 illustrates a schematic cross-sectional configuration of an imaging device (an imaging device 1B) according to Modification Example 2. In this way, a transparent electrode (a transparent electrode 14P) coupled to the first photoelectric converter 12P and a transparent electrode (a transparent electrode 14B) coupled to the second photoelectric converter 12B may be electrically separated from each other.

In this imaging device 1B, the separation film 13 is provided between the transparent electrode 14P and the transparent electrode 14B, and the transparent electrode 14P and the transparent electrode 14B are electrically separated from each other. The transparent electrode 14B is coupled to, for example, the same electric potential as that of the wiring line 22WB. Therefore, one (for example, a hole) of electric charges generated in the second photoelectric converter 12B is discharged to a predetermined electric potential through the wiring line 22WB, and the other electric charge (for example, an electron) is discharged to the predetermined electric potential through the transparent electrode 14B. The transparent electrode 14B may be coupled to an electric potential different from that of the wiring line 22WB.

Modification Example 3

Figure 14:
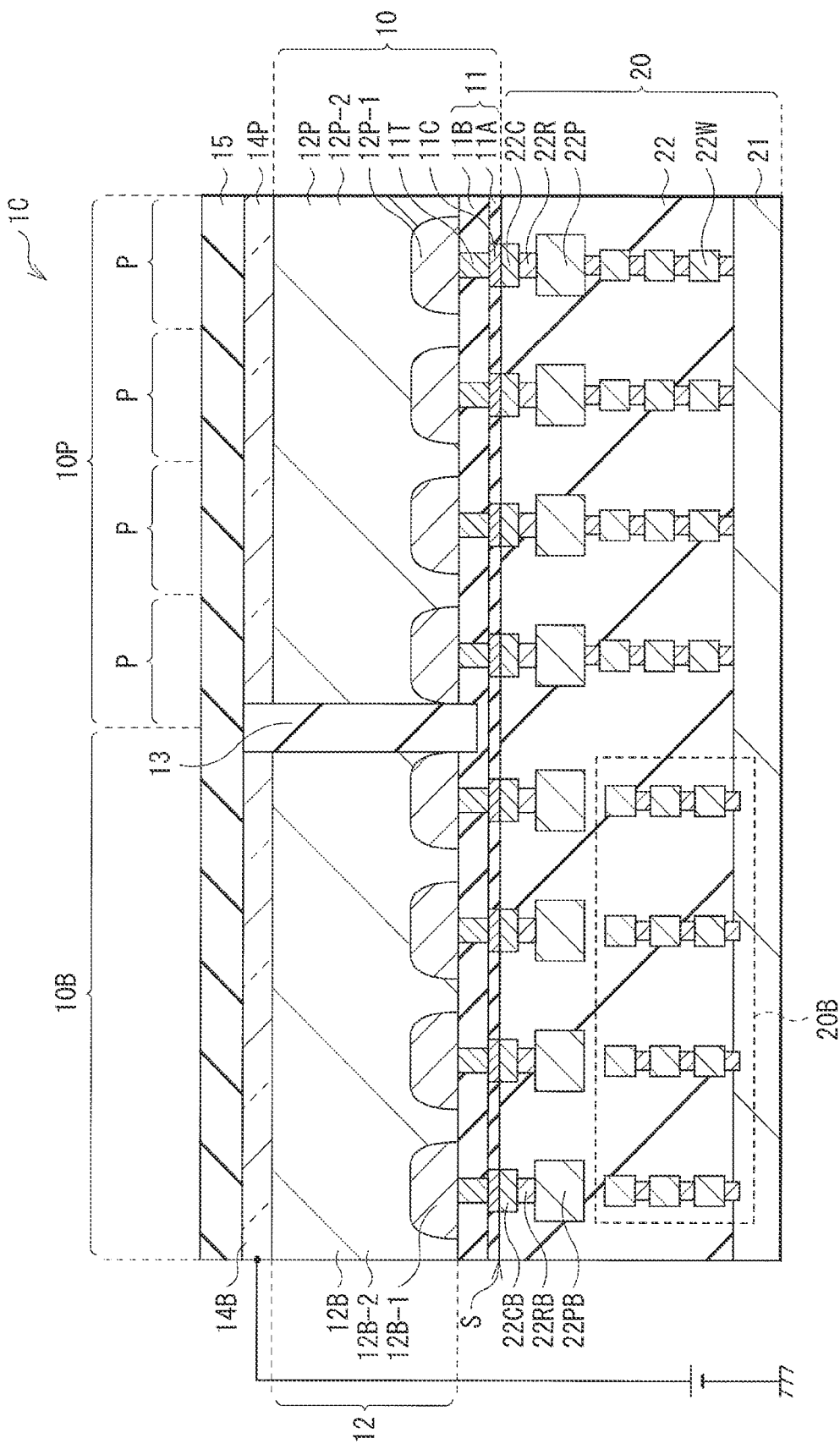
FIG. 14 is a cross-sectional view of a schematic configuration of an imaging device according to Modification Example 3.

FIG. 14 illustrates a schematic cross-sectional configuration of an imaging device (an imaging device 1C) according to Modification Example 3. In this way, the second photoelectric converter 12B may be supplied with a predetermined electric potential only from the transparent electrode 14B.

In this imaging device 1C, the through electrode 11TB of the outside-pixel region 10B is not coupled to a wiring line (the wiring line 22WB in FIG. 13). That is, the second photoelectric converter 12B is not supplied with an electric potential from the side of the circuit substrate 20. Therefore, an electric charge generated in the second photoelectric converter 12B is discharged to the predetermined electric potential through the transparent electrode 14B.

Modification Example 4

Figure 15:
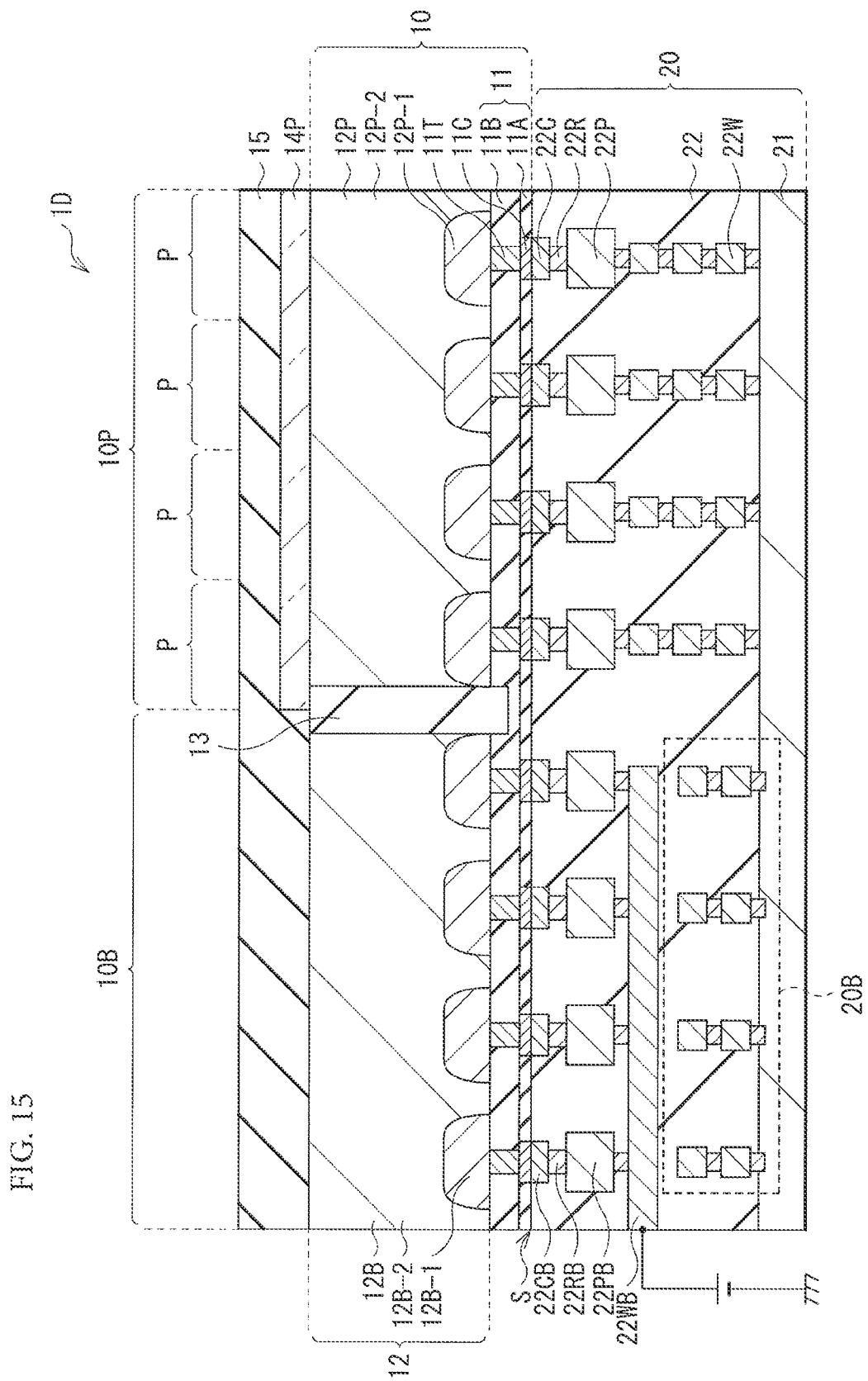
FIG. 15 is a cross-sectional view of a schematic configuration of an imaging device according to Modification Example 4.

FIG. 15 illustrates a schematic cross-sectional configuration of an imaging device (an imaging device 1D) according to Modification Example 4. In this way, in this way, only the first photoelectric converter 12P may be coupled to the transparent electrode 14P, and the second photoelectric converter 12B may be supplied with a predetermined electric potential from the side of the circuit substrate 20.

In this imaging device 1D, a transparent electrode (the transparent electrode 14B in FIG. 13) on the second photoelectric converter 12B is omitted. The second photoelectric converter 12B is coupled to the wiring line 22WB through the through electrode 11TB, etc. Therefore, an electric charge generated in the second photoelectric converter 12B is discharged to the predetermined electric potential through the wiring line 22WB.

Modification Example 5

Figure 16:
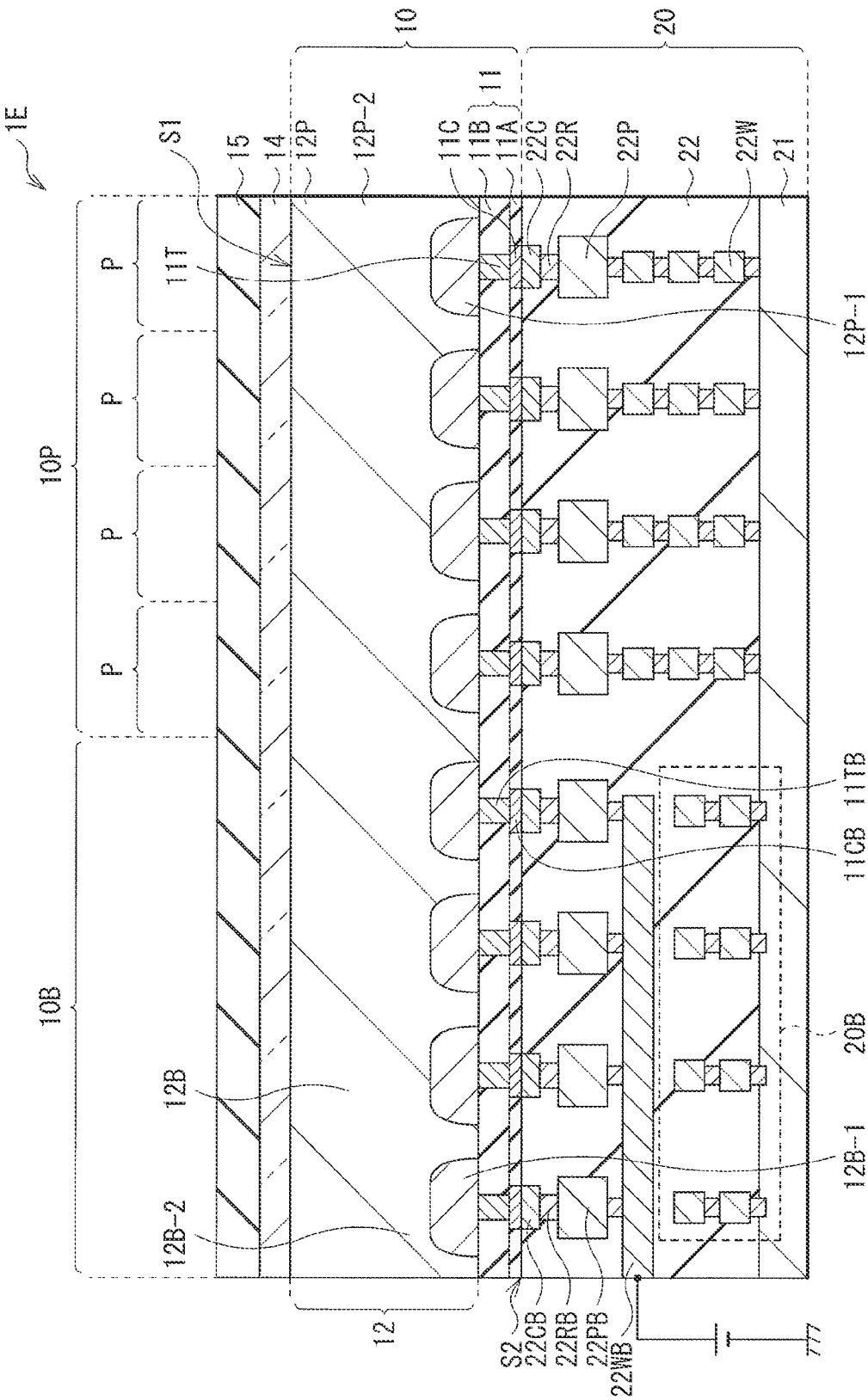
FIG. 16 is a cross-sectional view of a schematic configuration of an imaging device according to Modification Example 5.

FIG. 16 illustrates a schematic cross-sectional configuration of an imaging device (an imaging device 1E) according to Modification Example 5. In this way, the first photoelectric converter 12P and the second photoelectric converter 12B may be continuous without providing a separation film (the separation film 13) in the photoelectric conversion layer 12. Even in such a case, it is possible to process light generated in the outside-pixel region 10B and light that has entered the outside-pixel region 10B separately from light that has entered the pixel region 10P.

Second Embodiment

Figure 17:
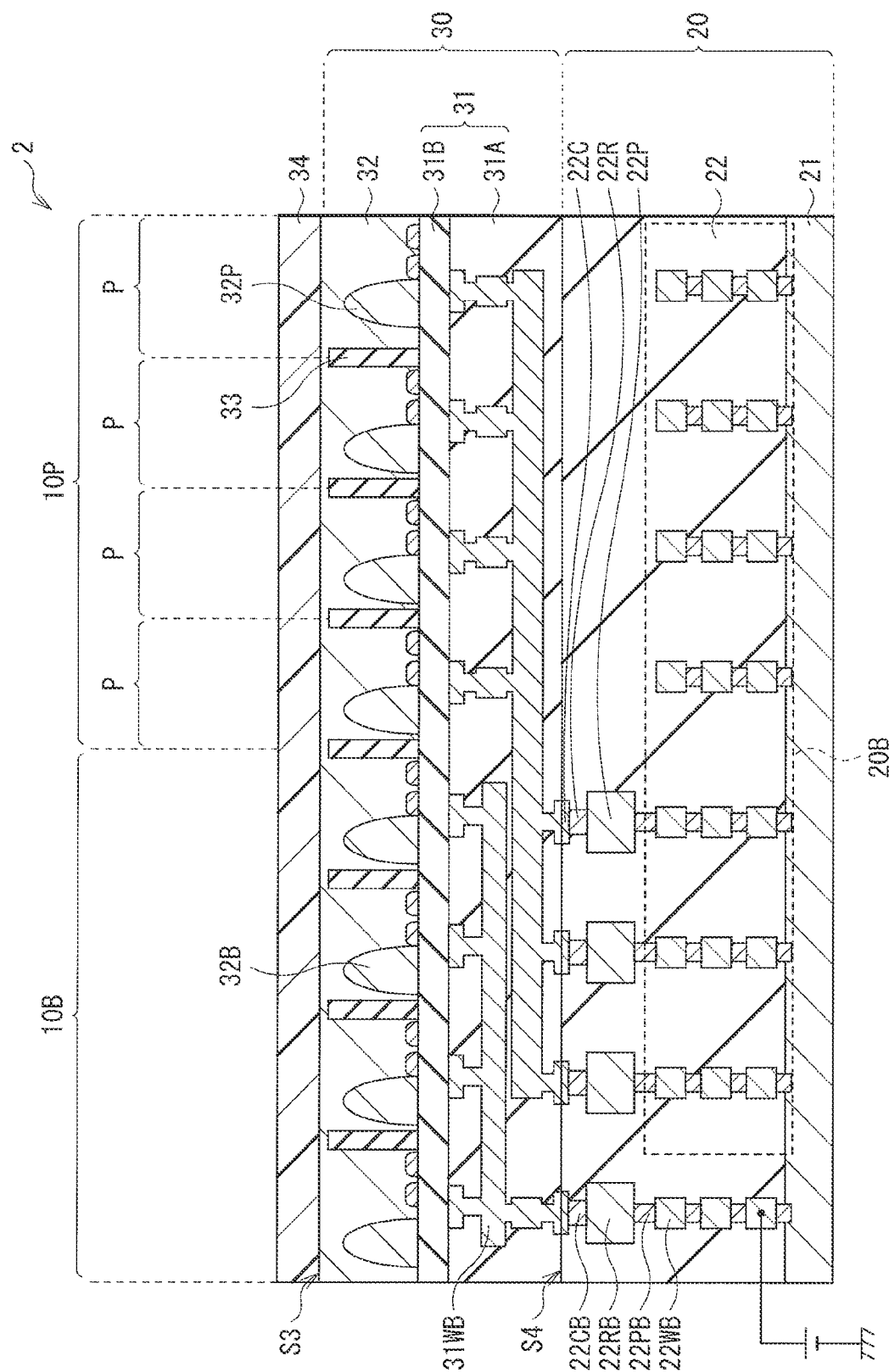
FIG. 17 is a cross-sectional view of a schematic configuration of an imaging device according to a second embodiment.

FIG. 17 illustrates a schematic cross-sectional configuration of an imaging device (an imaging device 2) according to a second embodiment. In the imaging device 2, a first photoelectric converter (a first photoelectric converter 32P) and a second photoelectric converter (a second photoelectric converter 32B) each include, for example, a photodiode having a p-n junction. Except for this point, the imaging device 2 has a similar configuration to that of the imaging device 1, and workings and effects are also similar.

The imaging device 2 has a stacked structure of the circuit substrate 20 and a photoelectric conversion substrate 30. A color filter layer 34 is provided on a light incident surface (a light incident surface S3) of the photoelectric conversion substrate 30. A joint surface (a joint surface S4) between the photoelectric conversion substrate 30 and the circuit substrate 20 is a surface opposed to the light incident surface S3. The photoelectric conversion substrate 30 includes a wiring layer 31 and a semiconductor layer 32 in this order from a position closer to the joint surface S4.

The wiring layer 31 includes, for example, a wiring layer 31A in contact with the circuit substrate 20, and a wiring layer 31B between the wiring layer 31A and the semiconductor layer 32. The wiring layer 31A is, for example, an inorganic insulating film of silicon oxide ($SiO_2$), etc. with a plurality of wiring lines (wiring lines 31W and 31WB, etc.) provided therein. The wiring line 31W provided in the wiring layer 31A serves to electrically couple the first photoelectric converter 32P and the ROIC to each other. A signal electric charge generated in the first photoelectric converter 32P moves to the circuit substrate 20 through the wiring line 31W and is read out by the ROIC. The wiring line 31WB serves to discharge an electric charge generated in the second photoelectric converter 32B to a predetermined electric potential. The wiring line 31WB is coupled to a predetermined electric potential such as a power source of the imaging device 2 or a ground (GND) electric potential through the wiring line 22WB provided in the circuit substrate 20. The wiring layer 31B is, for example, a semiconductor layer of polysilicon (poly-Si), etc. with a plurality of wiring lines provided therein.

The semiconductor layer 32 includes, for example, silicon (Si). This semiconductor layer 32 is provided with the first photoelectric converter 32P and the second photoelectric converter 32B. The first photoelectric converter 32P is provided in the pixel region 10P for each pixel P. The adjacent first photoelectric converters 32P are electrically separated from each other by a separation film 33. The plurality of second photoelectric converters 32B are provided in the outside-pixel region 10B, for example, at the same pitch as the first photoelectric converters 32P. In the imaging device 2 of the present embodiment, the second photoelectric converters 32B coupled to the predetermined electric potential are provided in the outside-pixel region 10B in this way: therefore, in a manner similar to those described above for the imaging device 1, it is possible to suppress the influences of the light E generated in the outside-pixel region 10B (see FIG. 8) and the light L1 that has entered the outside-pixel region 10B (see FIG. 9) on the pixel region 10P. For example, the adjacent second photoelectric converters 32B are also electrically separated from each other by the separation film 33. The separation film 33 is also provided between the first photoelectric converter 32P and the second photoelectric converter 32B that are adjacent to each other, and they are electrically separated from each other. The separation film 33 is provided in a thickness direction of the semiconductor layer 32. This separation film 33 includes, for example, an inorganic insulating material such as silicon oxide ($SiO_2$).

Figure 18:
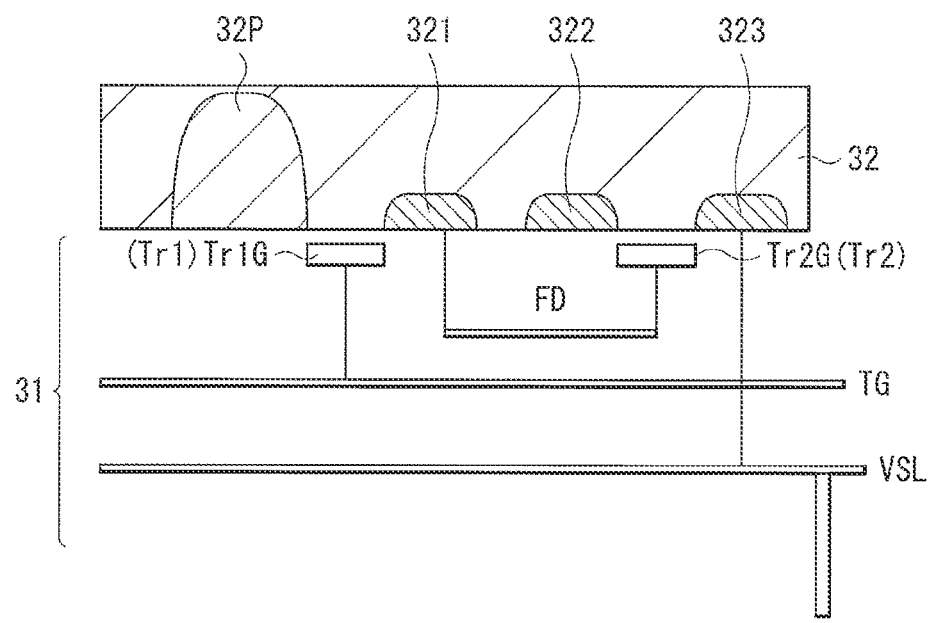
FIG. 18 is a cross-sectional view schematically illustrating an example of a configuration of a wiring layer and a semiconductor layer illustrated in FIG. 17.

FIG. 18 illustrates an example of a more detailed configuration of the wiring layer 31 and the semiconductor layer 32. In the semiconductor layer 32, in addition to the first photoelectric converters 32P and the second photoelectric converters 32B, for example, a floating diffusion (FD) 321, a power supply voltage (VDD) 322, and a diffusion region 323, etc. are provided near the wiring layer 31. The diffusion region 323 is, for example, a drain of a selection transistor, and is coupled to a vertical signal line VSL. The wiring layer 31 is provided with gate electrodes Tr1G and Tr2G, etc. of transistors (for example, a transfer transistor Tr1 and an amplification transistor Tr2 described later). The gate electrode Tr1G is, for example, a gate electrode of the transfer transistor Tr1. The gate electrode Tr2G is, for example, a gate electrode of the amplification transistor Tr2, and is electrically coupled to the FD 321.

Figure 19:
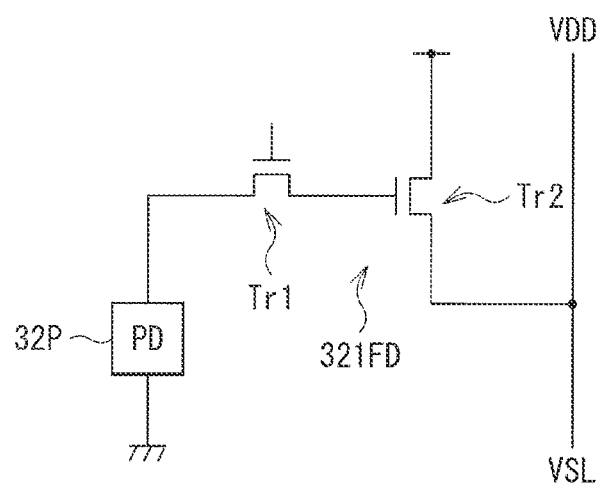
FIG. 19 illustrates an example of a pixel circuit of the imaging device illustrated in FIG. 17.

FIG. 19 illustrates an example of a pixel circuit of the imaging device 2. In this pixel circuit, a selection transistor and a reset transistor are omitted. The first photoelectric converter 32P is coupled to one terminal (for example, a source) of a source and a drain of the transfer transistor Tr1. The other terminal (for example, the drain) of the transfer transistor Tr1 is coupled to a gate of the amplification transistor Tr2 through the FD 321.

The color filter layer 34 includes, for example, a red filter, a green filter, a blue filter, and an IR filter, and these filters are disposed for each pixel P. Providing such a color filter layer 34 allows the imaging device 2 to obtain data of received light of a wavelength corresponding to its color array. The light incident surface S3 of the photoelectric conversion substrate 30 may be provided with an on-chip lens along with the color filter layer 34.

In the imaging device 2, when light (for example, light of a wavelength in the infrared region) enters the first photoelectric converter 12P through the color filter layer 34, this light is subjected to photoelectric conversion performed by the first photoelectric converter 32P that is a photodiode to generate an electron and a hole. One of these is accumulated, as a signal electric charge, in the first photoelectric converter 12P. This signal electric charge is transferred to the pixel circuit through the FD 321 at a predetermined timing, and is read out as a voltage signal by the vertical signal line VSL.

Also in the imaging device 2, in a manner similar to those described above for the imaging device 1, the second photoelectric converters 32B coupled to the predetermined electric potential are provided in the outside-pixel region 10B: therefore, it is possible to suppress the influences of the light E generated in the outside-pixel region 10B (FIG. 8) and the light L1 that has entered the outside-pixel region 10B (FIG. 9) on the pixel region 10P. Accordingly, it is possible to suppress degradation of the image quality.

Application Example

Figure 20:
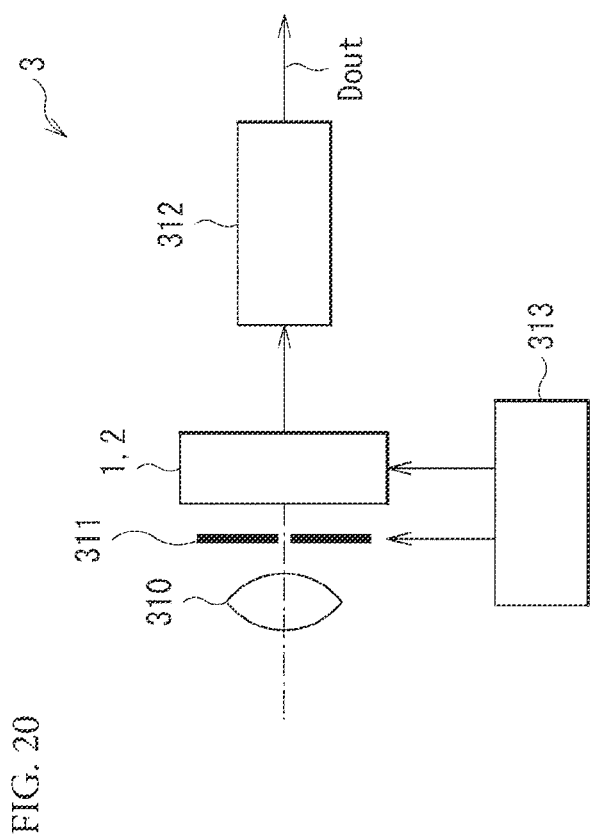
FIG. 20 is a functional block diagram illustrating an example of an electronic apparatus (a camera) using the imaging device illustrated in FIG. 1, etc.

The above-described imaging devices 1 and 2 are applicable to various types of electronic apparatuses, for example, such as a camera that allows for imaging of the infrared region. FIG. 20 illustrates a schematic configuration of an electronic apparatus 3 (a camera) as an example. This electronic apparatus 3 is, for example, a camera that is able to capture a still image or a moving image, and includes the imaging device 2, an optical system (an optical lens) 310, a shutter unit 311, a driver 313 that drives the imaging device 2 and the shutter unit 311, and a signal processor 312.

The optical system 310 guides image light (incident light) from an object to the imaging device 2. This optical system 310 may include a plurality of optical lenses. The shutter unit 311 controls a period in which the imaging device 2 is irradiated with light and a period in which the light is blocked. The driver 313 controls a transfer operation of the imaging device 2 and a shutter operation of the shutter unit 311. The signal processor 312 performs various types of signal processing on a signal outputted from the imaging device 2. An image signal Dout having been subjected to the signal processing is stored in a storage medium such as a memory, or is outputted to a monitor or the like.

Furthermore, the imaging devices 1 and 2 described in the present embodiments, etc. are also applicable to below-described electronic apparatuses (a capsule endoscope and a mobile body such as a vehicle).

Practical Application Example 1 (Endoscopic Surgery System)

The technology according to the present disclosure is applicable to various products. For example, the technology according to the present disclosure may be applied to an endoscopic surgery system.

Figure 21:
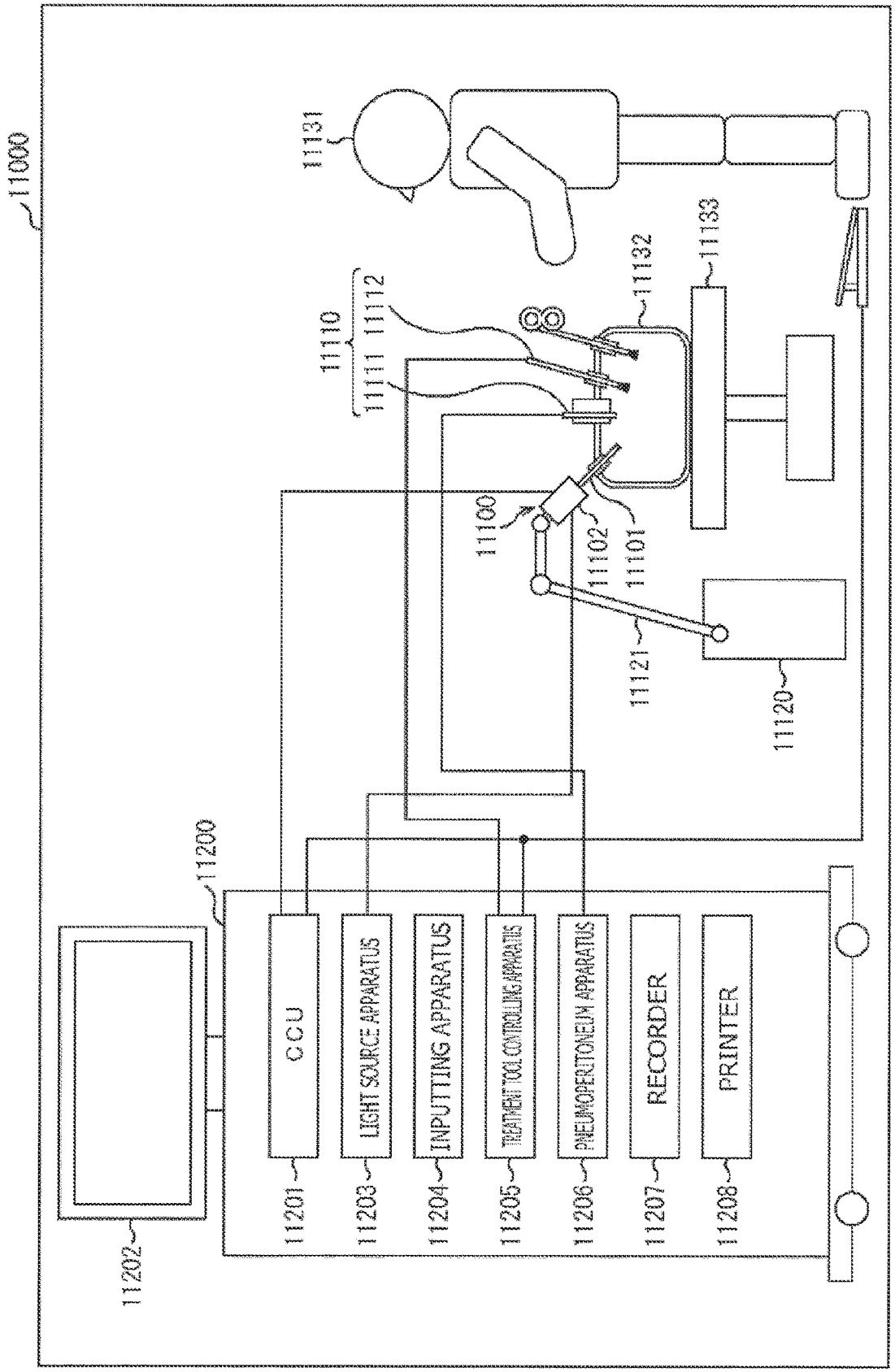
FIG. 21 is a view depicting an example of a schematic configuration of an endoscopic surgery system.

FIG. 21 is a view depicting an example of a schematic configuration of an endoscopic surgery system to which the technology according to an embodiment of the present disclosure (present technology) can be applied.

In FIG. 21, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

Figure 22:
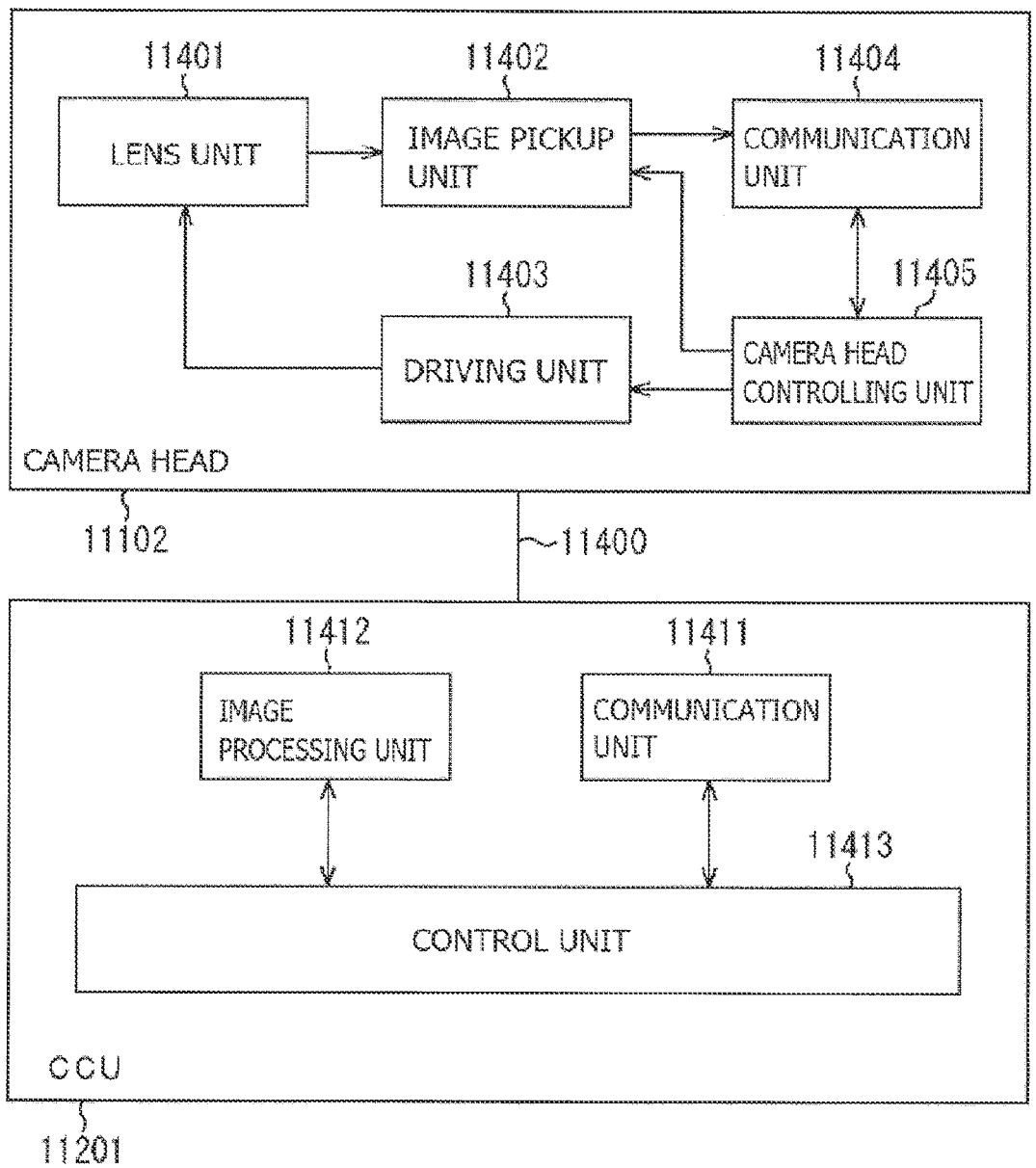
FIG. 22 is a block diagram depicting an example of a functional configuration of a camera head and a camera control unit (CCU).

FIG. 22 is a block diagram depicting an example of a functional configuration of the camera head 11102 and the CCU 11201 depicted in FIG. 21.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

The description has been given above of one example of the endoscopic surgery system, to which the technology according to the present disclosure is applicable. The technology according to the present disclosure may be applied to the image pickup unit 11402 of the configurations described above. Applying the technology according to the present disclosure to the image pickup unit 11402 makes it possible to acquire a finer operative image. Hence, it is possible for the surgeon to confirm the surgical region with certainty.

It is to be noted that the description has been given above of the endoscopic surgery system as one example. The technology according to the present disclosure may be applied to any other medical system such as a micrographic surgery system, for example.

Practical Application Example 2 (Mobile Body)

The technology according to an embodiment of the present disclosure (present technology) is applicable to various products. For example, the technology according to an embodiment of the present disclosure may be achieved in the form of an apparatus to be mounted to a mobile body of any kind. Non-limiting examples of the mobile body may include an automobile, an electric vehicle, a hybrid electric vehicle, a motorcycle, a bicycle, any personal mobility device, an airplane, an unmanned aerial vehicle (drone), a vessel, and a robot.

Figure 23:
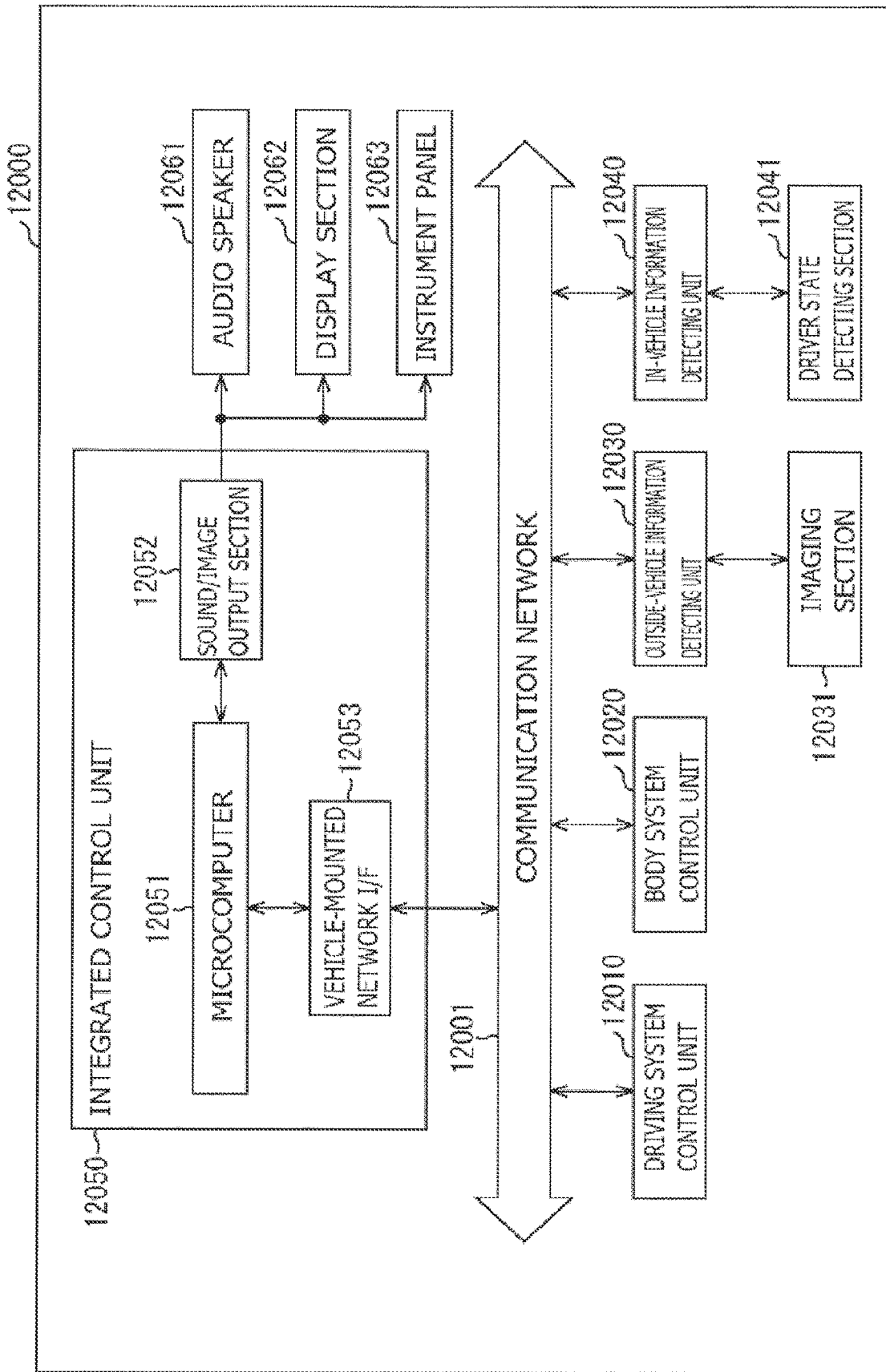
FIG. 23 is a block diagram depicting an example of schematic configuration of a vehicle control system.

FIG. 23 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 23, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 23, an audio speaker 12061, a display section 12062, and an instrument panel 12063 are illustrated as the output device. The display section 12062 may, for example, include at least one of an on-board display and a head-up display.

Figure 24:
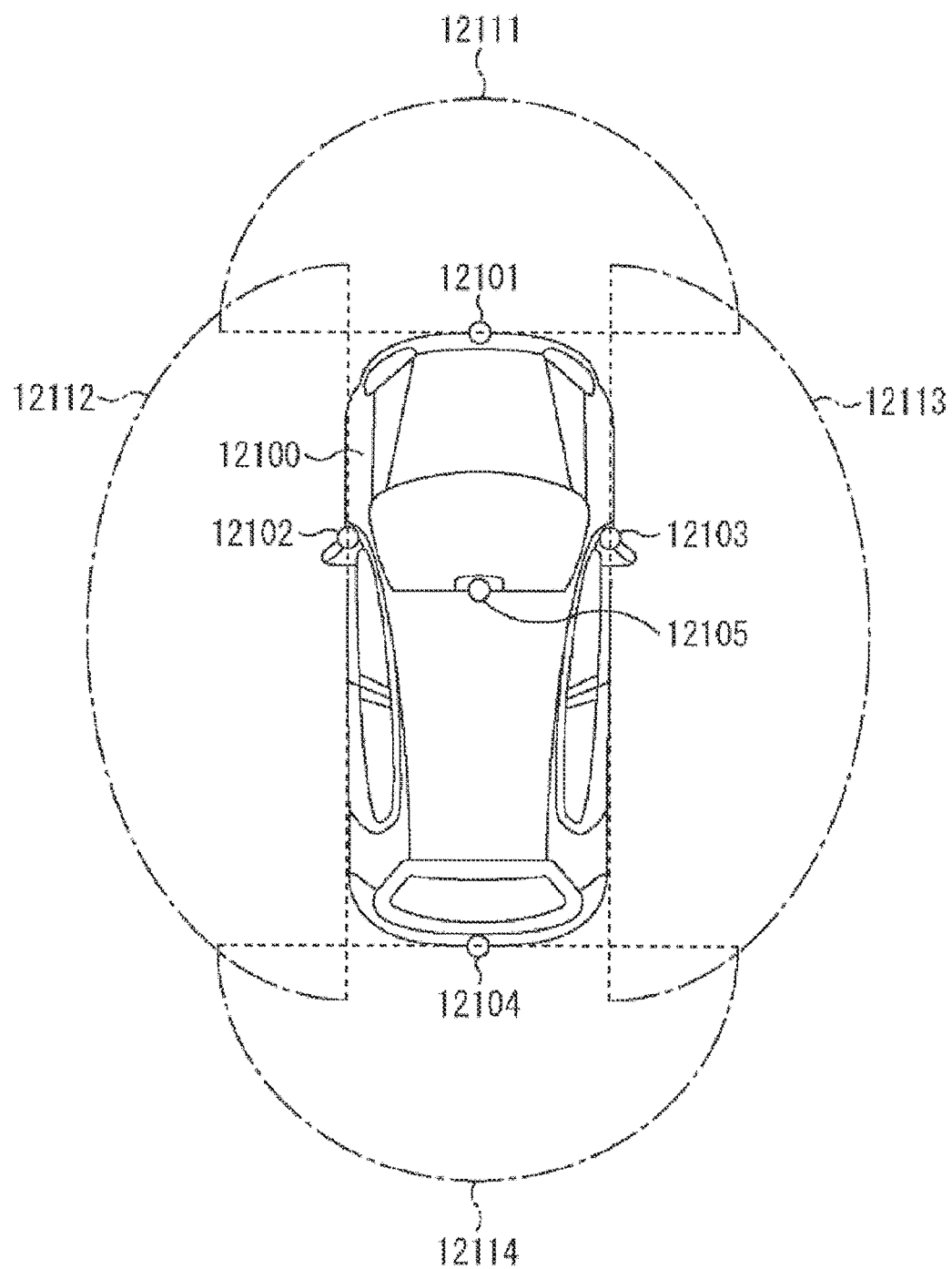
FIG. 24 is a diagram of assistance in explaining an example of installation positions of an outside-vehicle information detecting section and an imaging section.

FIG. 24 is a diagram depicting an example of the installation position of the imaging section 12031.

In FIG. 24, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 24 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

In the foregoing, the description has been given of one example of the vehicle control system, to which the technology according to the present disclosure is applicable. The technology according to the present disclosure may be applied to the imaging section 12031 of the configurations described above. Applying the technology according to the present disclosure to the imaging section 12031 makes it possible to obtain a captured image which is easier to see. Hence, it is possible to reduce the fatigue of the driver.

The present disclosure has been described above with reference to the embodiments, the modification examples, the application examples, and practical application examples; however, the present disclosure is not limited to the above-described embodiments, etc., and may be modified in a variety of ways. For example, respective layer configurations of the imaging devices described in the above-described embodiments are merely exemplary, and may further include any other layer. Furthermore, the materials and thicknesses of the respective layers are merely exemplary as well, and are not limited to those described above.

Figure 25:
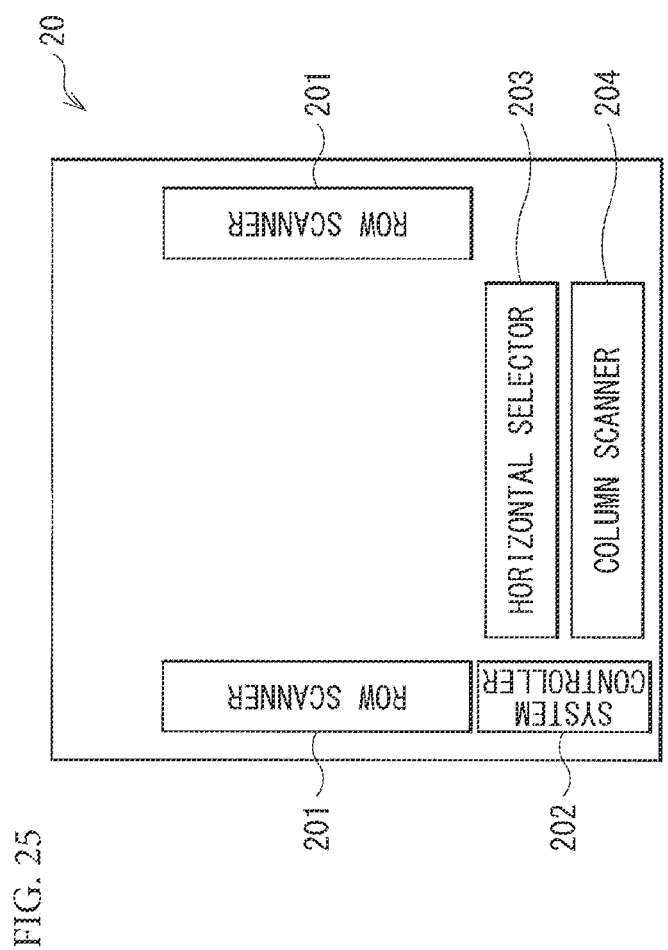
FIG. 25 is a plan view of another example of a configuration of a row scanner illustrated in FIG. 2.

Moreover, the circuit configurations described in the above-described embodiments, etc. are merely exemplary: the configurations, layouts, etc. of the respective circuits are not limited to those described above. As illustrated in FIG. 25, the row scanner 201 may be disposed on each of two sides of the circuit substrate 20.

Figure 26A:
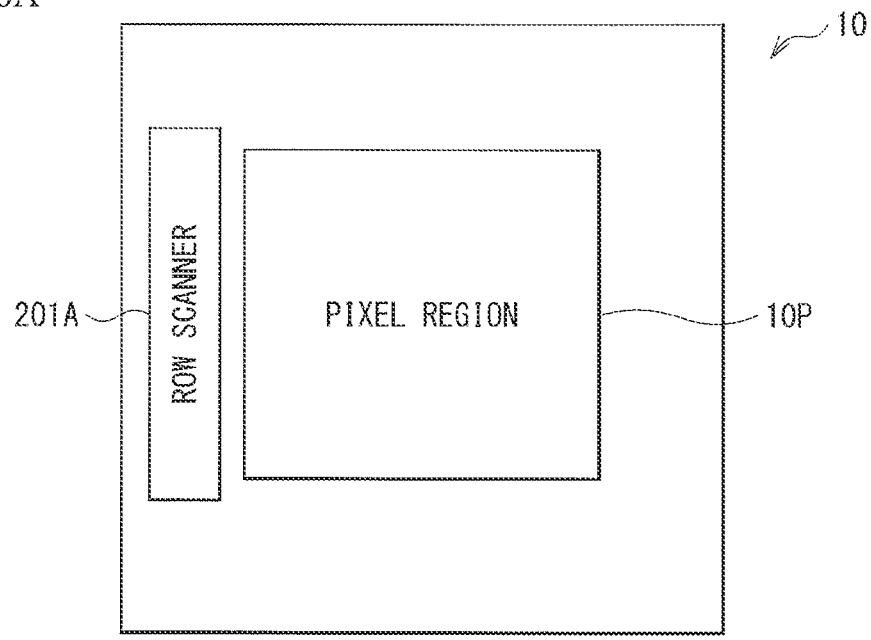
FIG. 26A is a plan view of another example (1) of a configuration of a semiconductor substrate illustrated in FIG. 3.
Figure 26B:
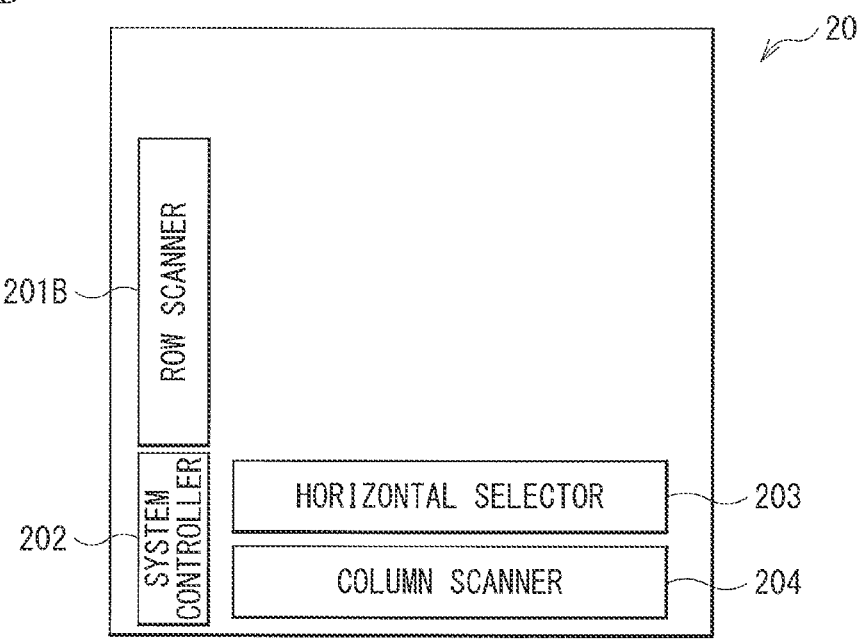
FIG. 26B is a plan view of another example (1) of a configuration of a circuit substrate illustrated in FIG. 3.
Figure 27A:
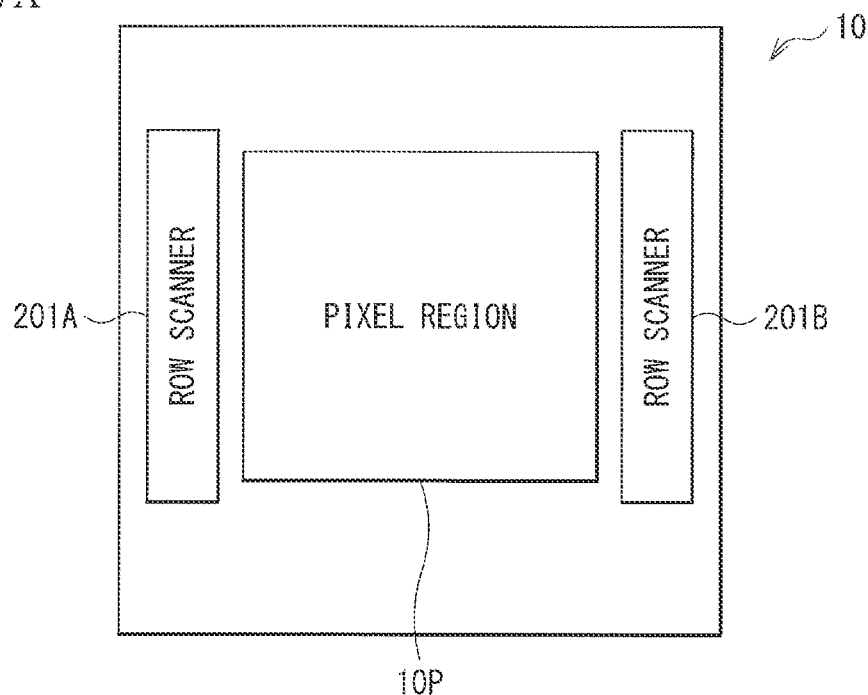
FIG. 27A is a plan view of another example (2) of the configuration of the semiconductor substrate illustrated in FIG. 3.
Figure 27B:
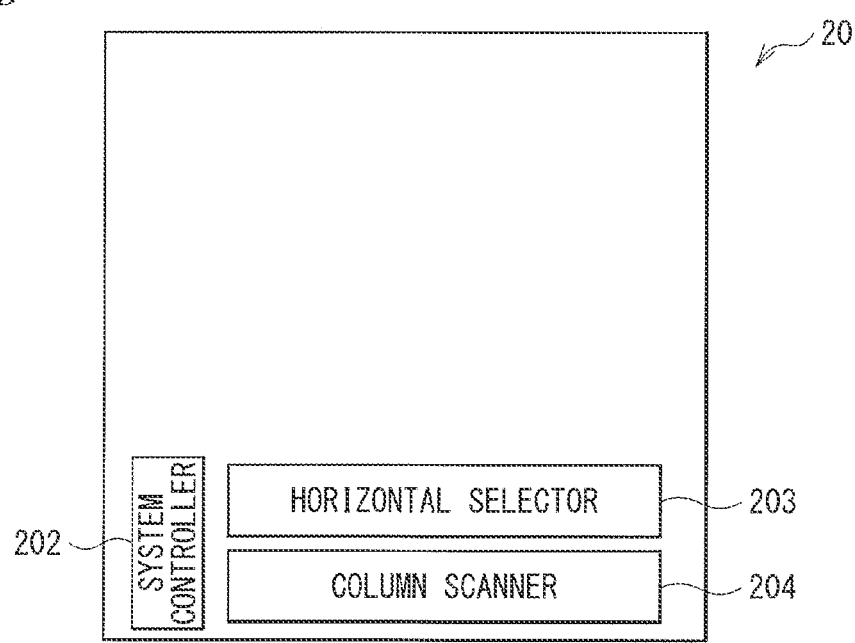
FIG. 27B is a plan view of another example (2) of the configuration of the circuit substrate illustrated in FIG. 3.

Furthermore, a circuit may be provided on the semiconductor substrate 10. As illustrated in FIGS. 26A and 26B, the row scanner may be divided to provide a row scanner 201A on the semiconductor substrate 10 and a row scanner 201B in the circuit substrate 20. As illustrated in FIGS. 27A and 27B, the row scanners 201A and 201B (or the row scanners 201) may be provided on the semiconductor substrate 10 without providing any row scanners in the circuit substrate 20. A circuit section having a function other than the row scanner may be divided, or may be provided on the semiconductor substrate 10.

The effects described in the above-described embodiments, etc. are merely exemplary, and may be other effects or may further include other effects.

It is to be noted that the present disclosure may have the following configurations.

(1)
An imaging device including:
a pixel region including a first photoelectric converter:
an outside-pixel region including a second photoelectric converter coupled to a predetermined electric potential: and
a circuit substrate having one surface on which the first photoelectric converter and the second photoelectric converter are provided, the circuit substrate including a peripheral circuit electrically coupled to the first photoelectric converter.

(2)
The imaging device according to (1), in which the first photoelectric converter and the second photoelectric converter are electrically separated from each other.

(3)
The imaging device according to (1) or (2), in which a constituent material of the second photoelectric converter is same as a constituent material of the first photoelectric converter.

(4)
The imaging device according to any one of (1) to (3), in which the second photoelectric converter is provided in a region that overlaps the peripheral circuit in a plan view.

(5)
The imaging device according to any one of (1) to (4), in which the second photoelectric converter has at least a same sensitivity wavelength range as a sensitivity wavelength range of the first photoelectric converter.

(6)
The imaging device according to any one of (1) to (5), in which the first photoelectric converter and the second photoelectric converter each absorb light of a wavelength in an infrared region and generate an electric charge.

(7)
The imaging device according to any one of (1) to (6), in which the first photoelectric converter and the second photoelectric converter each include a compound semiconductor.

(8)
The imaging device according to (7), in which the first photoelectric converter and the second photoelectric converter each include a group III-V semiconductor.

(9)
The imaging device according to (8), in which the group III-V semiconductor includes InGaAs.

(10)
The imaging device according to any one of (7) to (9), further including, for each pixel, a first electrically-conductive type region to which a signal electric charge generated in the first photoelectric converter moves.

(11)
The imaging device according to (10), in which the circuit substrate is provided with a pixel circuit for each pixel, and the first electrically-conductive type region is electrically coupled to the pixel circuit.

(12)
The imaging device according to any one of (7) to (11), further including a first electrode that is opposed to the circuit substrate, with the first photoelectric converter being interposed therebetween.

(13)
The imaging device according to (12), further including a second electrode that is opposed to the circuit substrate, with the second photoelectric converter being interposed therebetween.

(14)
The imaging device according to (13), in which the first electrode and the second electrode are integrally provided.

(15)
The imaging device according to (13), in which the first electrode and the second electrode are provided to be electrically separated from each other.

(16)
The imaging device according to any one of (1) to (5), in which the first photoelectric converter and the second photoelectric converter each include a photodiode.

(17)
The imaging device according to any one of (1) to (16), in which the predetermined electric potential includes a power source or a ground electric potential.

(18)
An electronic apparatus including an imaging device, the imaging device including
a pixel region including a first photoelectric converter,
an outside-pixel region including a second photoelectric converter coupled to a predetermined electric potential, and
a circuit substrate having one surface on which the first photoelectric converter and the second photoelectric converter are provided, the circuit substrate including a peripheral circuit electrically coupled to the first photoelectric converter.

This application claims the benefit of Japanese Priority Patent Application JP2017-30375 filed with the Japan Patent Office on Feb. 21, 2017, the entire contents of which are incorporated herein by reference.

It should be understood by those skilled in the art that various modifications, combinations, sub-combinations, and alterations may occur depending on design requirements and other factors insofar as they are within the scope of the appended claims or the equivalents thereof.

What is claimed is:
1. An imaging device comprising:
a pixel region including a first photoelectric converter;
an outside-pixel region including a second photoelectric converter coupled to a predetermined electric potential; and
a circuit substrate having one surface on which the first photoelectric converter and the second photoelectric converter are provided, the circuit substrate including a peripheral circuit electrically coupled to the first photoelectric converter.

2. The imaging device according to claim 1, wherein the first photoelectric converter and the second photoelectric converter are electrically separated from each other.

3. The imaging device according to claim 1, wherein a constituent material of the second photoelectric converter is same as a constituent material of the first photoelectric converter.

4. The imaging device according to claim 1, wherein the second photoelectric converter is provided in a region that overlaps the peripheral circuit in a plan view.

5. The imaging device according to claim 1, wherein the second photoelectric converter has at least a same sensitivity wavelength range as a sensitivity wavelength range of the first photoelectric converter.

6. The imaging device according to claim 1, wherein the first photoelectric converter and the second photoelectric converter each absorb light of a wavelength in an infrared region and generate an electric charge.

7. The imaging device according to claim 1, wherein the first photoelectric converter and the second photoelectric converter each include a compound semiconductor.

8. The imaging device according to claim 7, wherein the first photoelectric converter and the second photoelectric converter each include a group III-V semiconductor.

9. The imaging device according to claim 8, wherein the group III-V semiconductor comprises InGaAs.

10. The imaging device according to claim 7, further comprising, for each pixel, a first electrically-conductive type region to which a signal electric charge generated in the first photoelectric converter moves.

11. The imaging device according to claim 10, wherein the circuit substrate is provided with a pixel circuit for each pixel, and the first electrically-conductive type region is electrically coupled to the pixel circuit.

12. The imaging device according to claim 7, further comprising a first electrode that is opposed to the circuit substrate, with the first photoelectric converter being interposed therebetween.

13. The imaging device according to claim 12, further comprising a second electrode that is opposed to the circuit substrate, with the second photoelectric converter being interposed therebetween.

14. The imaging device according to claim 13, wherein the first electrode and the second electrode are integrally provided.

15. The imaging device according to claim 13, wherein the first electrode and the second electrode are provided to be electrically separated from each other.

16. The imaging device according to claim 1, wherein the first photoelectric converter and the second photoelectric converter each comprise a photodiode.

17. The imaging device according to claim 1, wherein the predetermined electric potential comprises a power source or a ground electric potential.

18. An electronic apparatus comprising an imaging device, the imaging device including
a pixel region including a first photoelectric converter,
an outside-pixel region including a second photoelectric converter coupled to a predetermined electric potential, and
a circuit substrate having one surface on which the first photoelectric converter and the second photoelectric converter are provided, the circuit substrate including a peripheral circuit electrically coupled to the first photoelectric converter.

* * * * *